(12) United States Patent
Shahinpoor et al.

(10) Patent No.: US 7,090,696 B2
(45) Date of Patent: *Aug. 15, 2006

(54) SURGICAL CORRECTION OF HUMAN EYE REFRACTIVE ERRORS BY ACTIVE COMPOSITE ARTIFICIAL MUSCLE IMPLANTS

(75) Inventors: Mohsen Shahinpoor, Albuquerque, NM (US); Parsa Shahinpoor, Albuquerque, NM (US); David Soltanpour, Larchmont, NY (US)

(73) Assignee: Environmental Robots, Inc., Albuquerque, NM (US)

( * ) Notice: Subject to any disclaimer, the term of this patent is extended or adjusted under 35 U.S.C. 154(b) by 324 days.

This patent is subject to a terminal disclaimer.

(21) Appl. No.: 10/345,583

(22) Filed: Jan. 16, 2003

(65) Prior Publication Data

US 2003/0139808 A1    Jul. 24, 2003

Related U.S. Application Data

(63) Continuation-in-part of application No. 09/633,023, filed on Aug. 4, 2000, now Pat. No. 6,511,508.

(51) Int. Cl.
*A61F 2/14* (2006.01)
(52) U.S. Cl. .................................... 623/4.1
(58) Field of Classification Search ............ 623/4.1, 623/5.12, 6.64, 14.13, 905, FOR. 103, 3.11; 600/37; 601/153; 607/53, 54
See application file for complete search history.

(56) References Cited

U.S. PATENT DOCUMENTS

| 4,549,529 A | 10/1985 | White |
| 4,731,076 A * | 3/1988 | Noon et al. ............ 623/3.22 |
| 4,961,744 A | 10/1990 | Kilmer et al. |
| 5,147,284 A | 9/1992 | Fedorov et al. |
| 5,250,167 A | 10/1993 | Adolf et al. |
| 5,300,118 A | 4/1994 | Silvestrini et al. |
| 5,354,331 A | 10/1994 | Schachar |
| 5,389,222 A | 2/1995 | Shahinpoor |
| 5,465,737 A | 11/1995 | Schachar |
| 5,489,299 A | 2/1996 | Schachar |
| 5,503,165 A | 4/1996 | Schachar |
| 5,529,076 A | 6/1996 | Schachar |
| 5,722,952 A | 3/1998 | Schachar |
| 5,735,607 A | 4/1998 | Shahinpoor et al. |
| 5,766,171 A | 6/1998 | Silvestrini |
| 5,782,894 A | 7/1998 | Israel |

(Continued)

FOREIGN PATENT DOCUMENTS

FR          2354752          1/1978

(Continued)

*Primary Examiner*—David H. Willse
(74) *Attorney, Agent, or Firm*—Dennis F. Armijo

(57) ABSTRACT

Correction of eye refractive errors like presbyopia, hyperopia, myopia, and astigmatism using either pre-tensioned or transcutaneously energized artificial muscle implants to change the axial length and anterior curvatures of the eye globe by bringing the retina/macula region to coincide with the focal point. The implants are scleral constrictor bands, segments or ribs for inducing accommodation of a few diopters, to correct refractive errors on demand or automatically. The implant comprises an active sphinctering band encircling the sclera, implanted under the conjunctiva and under the extraocular muscles to uniformly constrict the eye globe, to induce active temporary myopia (hyperopia) by increasing(decreasing) the length and curvature of the globe. Multiple and specially designed constrictor bands enable surgeons to correct astigmatism. The artificial muscles comprise materials such as composite magnetic shape memory (MSM), heat shrink, shape memory alloy-silicone rubber, electroactive ionic polymeric artificial muscles or etectrochemically contractile ionic polymers bands.

4 Claims, 22 Drawing Sheets

| U.S. PATENT DOCUMENTS | | | |
|---|---|---|---|
| 5,821,664 A | 10/1998 | Shahinpoor | |
| 5,824,086 A | 10/1998 | Silvestrini et al. | |
| 5,888,243 A | 3/1999 | Silvestrini | |
| 6,006,756 A | 12/1999 | Shadduck | |
| 6,007,578 A | 12/1999 | Schachar | |
| 6,051,023 A | 4/2000 | Kilmer et al. | |

FOREIGN PATENT DOCUMENTS

| FR | 2 772 971 A1 * | 6/1999 |
|---|---|---|
| SU | 1725875 A | 4/1992 |
| WO | WO97/49354 | 12/1997 |

* cited by examiner

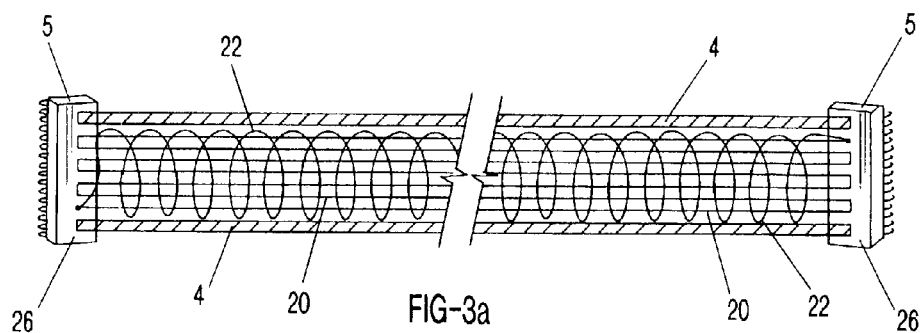
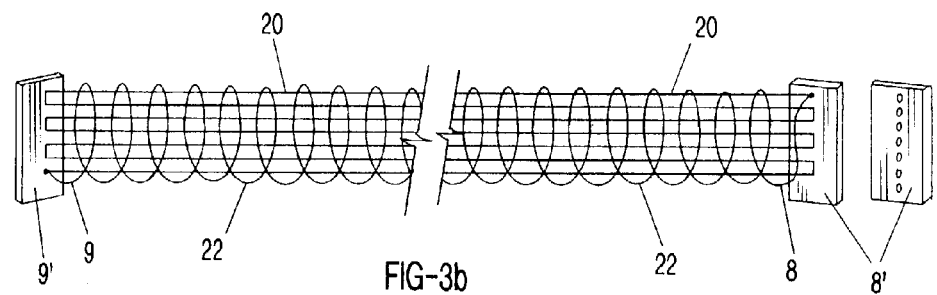
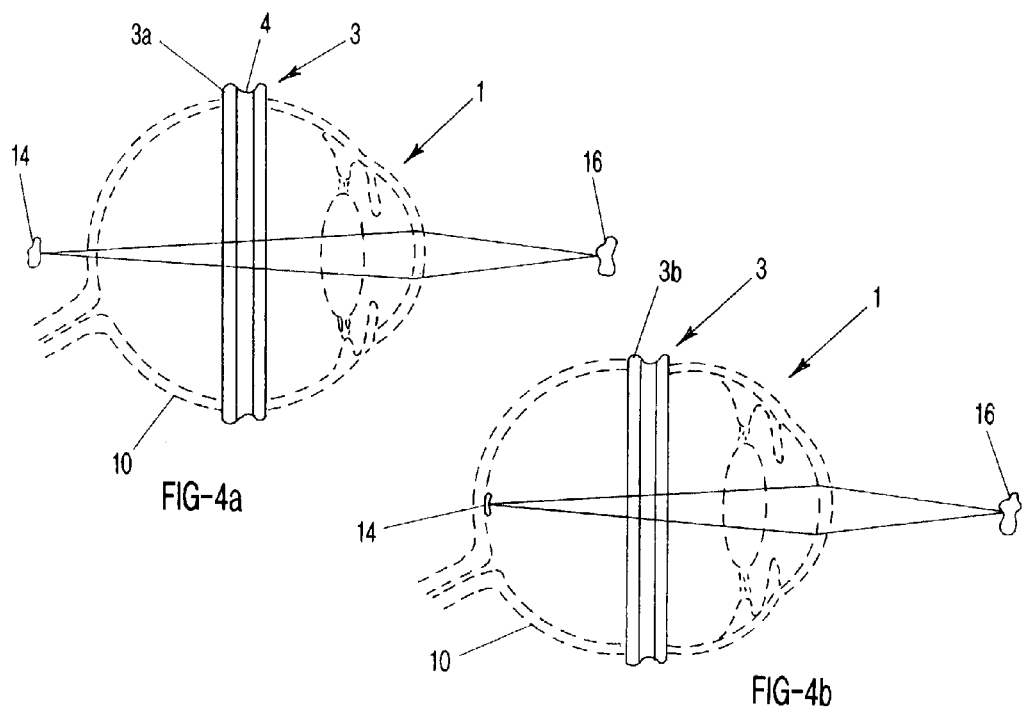

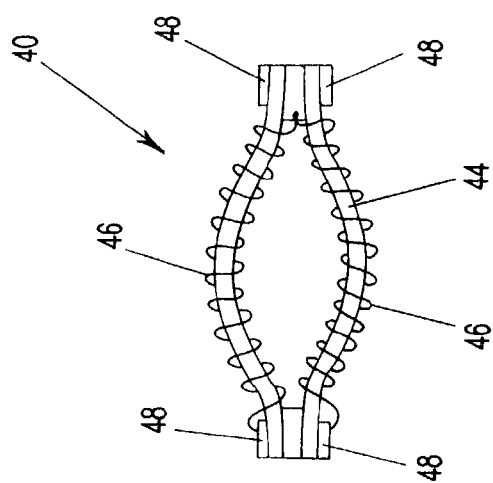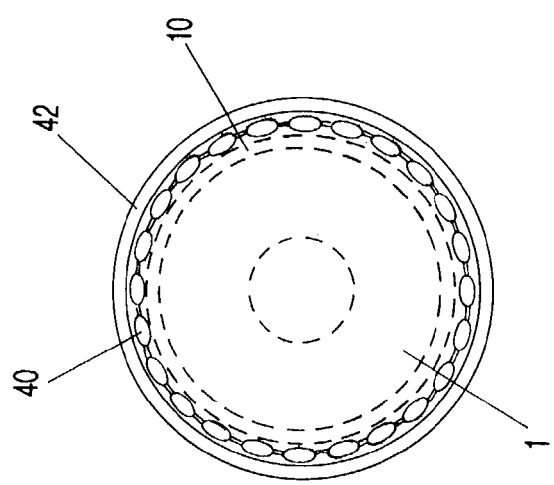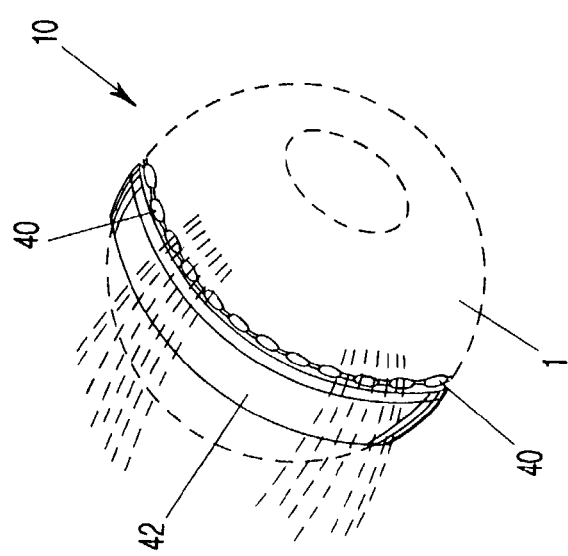

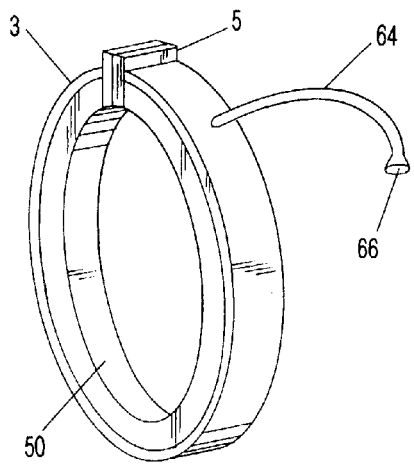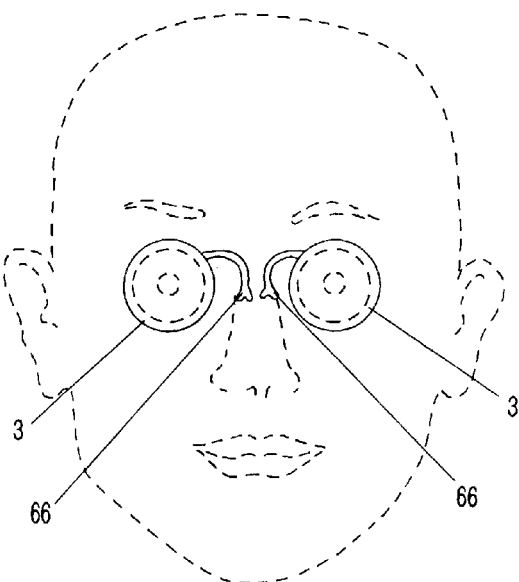
FIG-8a　　　　　　　　　　　　FIG-8b
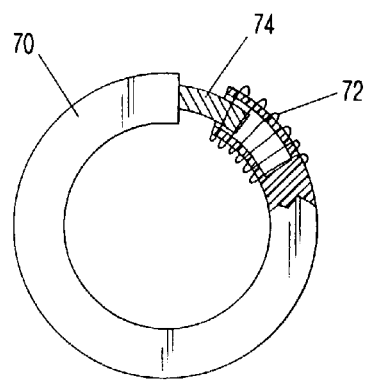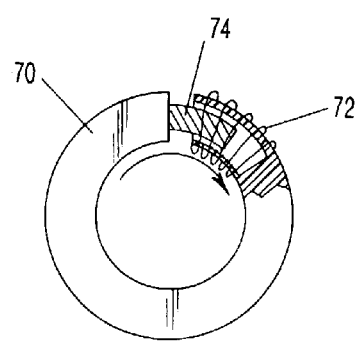
FIG-9a　　　　　　　　　　　　FIG-9b

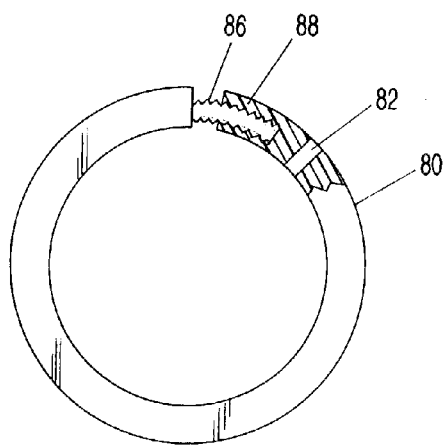
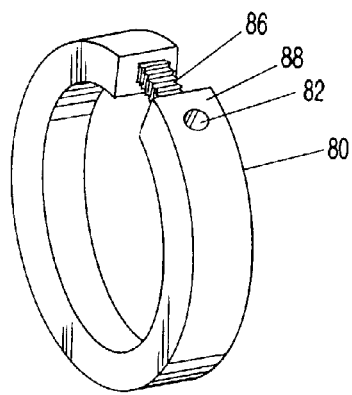
FIG-10a  FIG-10b
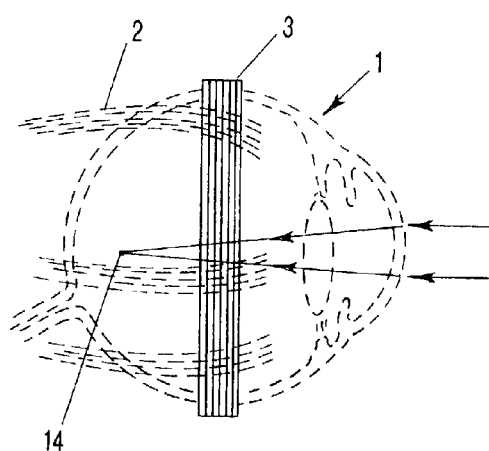
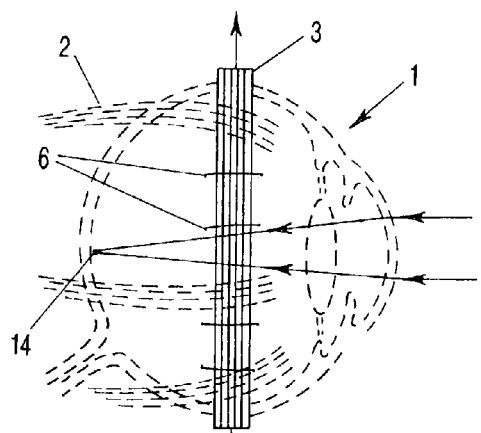
FIG-11a  FIG-11b
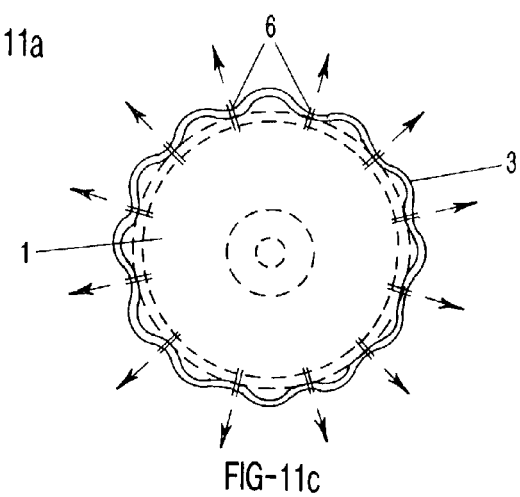
FIG-11c (a)          (b)

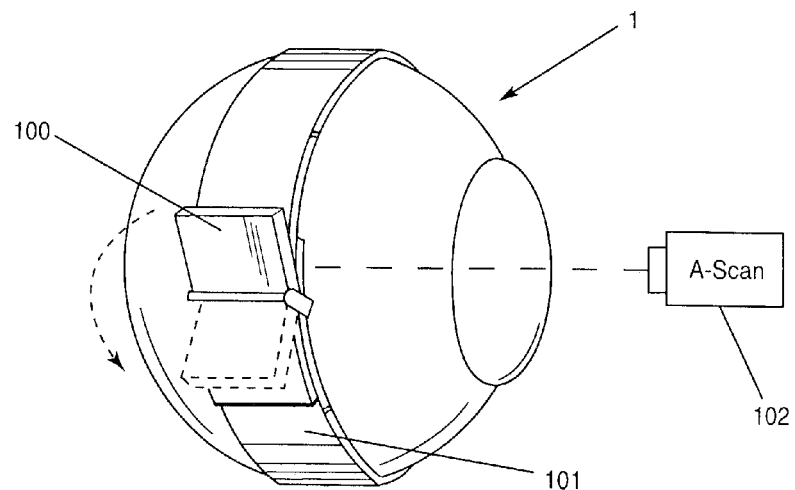
FIG-15 (a)
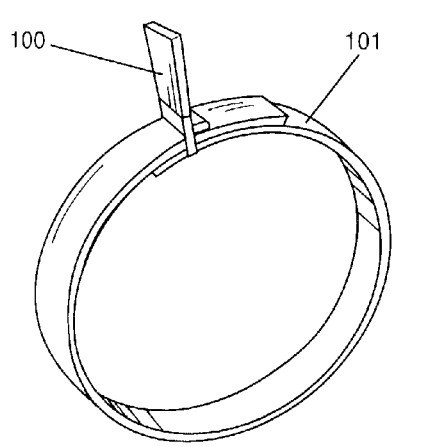
FIG-15' (a)
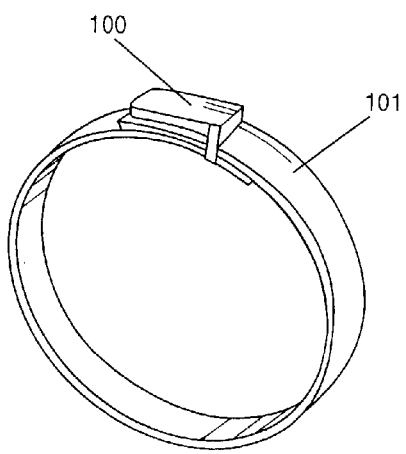
FIG-15" (a)

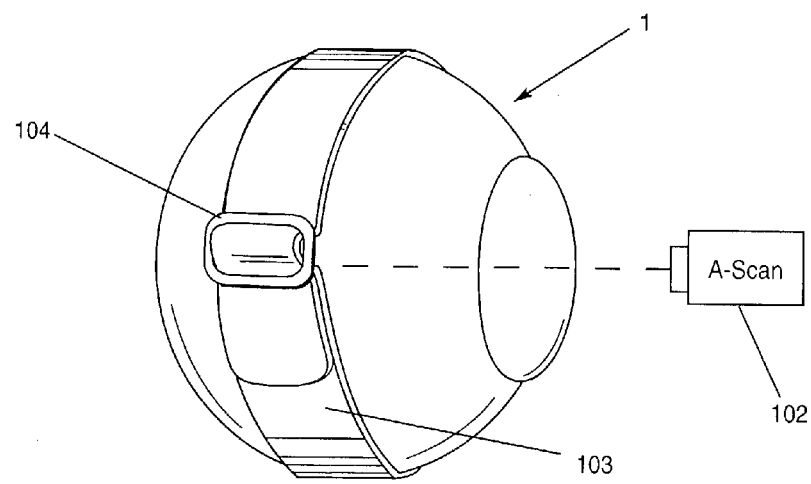
FIG-15 (b)
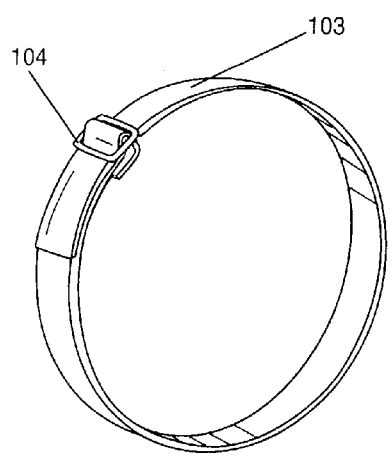
FIG-15' (b)
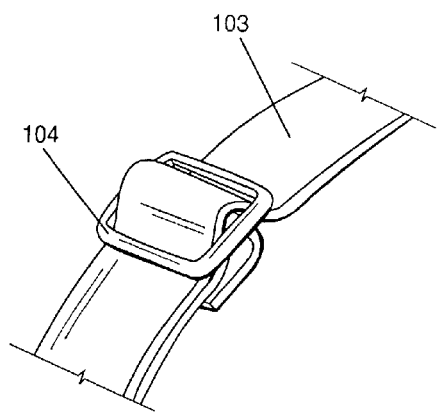
FIG-15" (b)

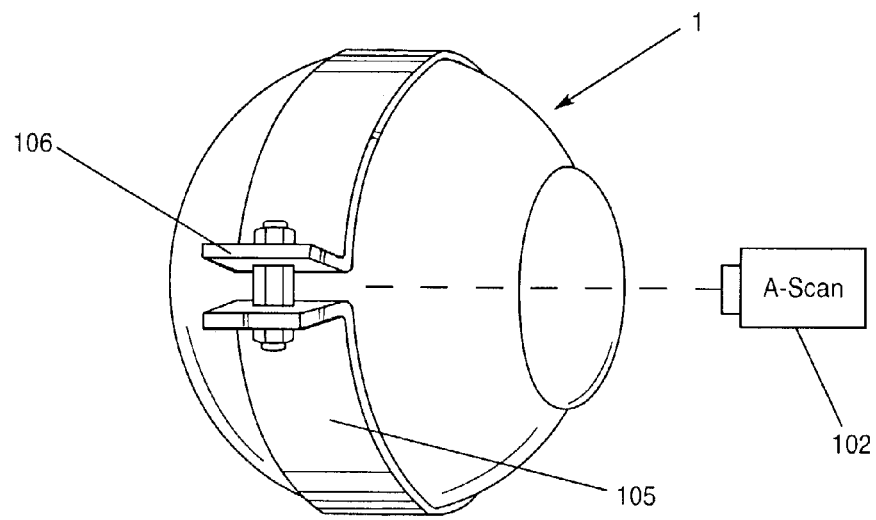
FIG-15 (c)
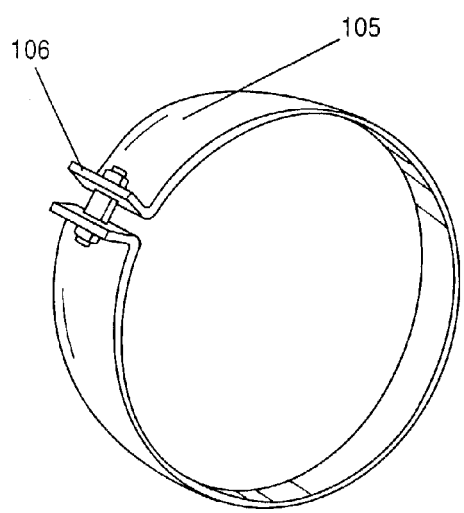
FIG-15' (c)
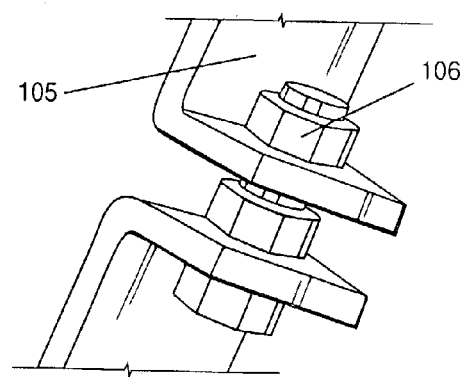
FIG-15" (c)

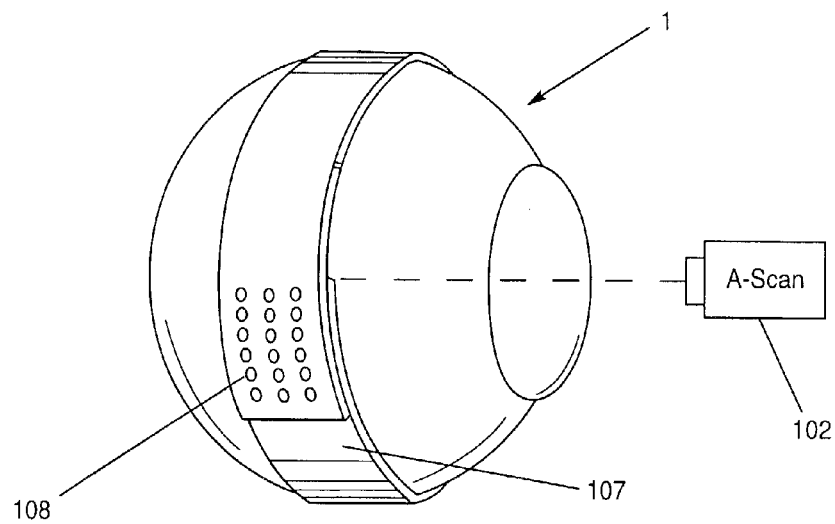
FIG-15 (d)
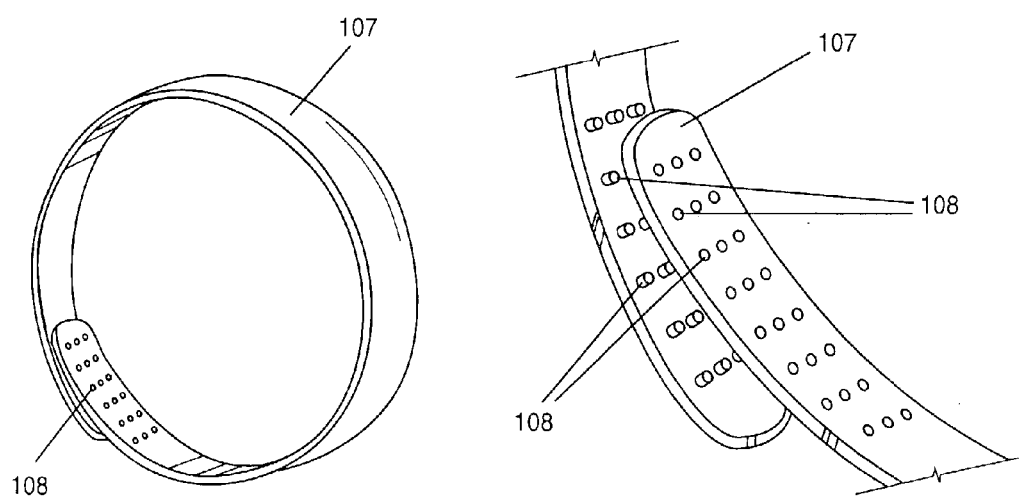
FIG-15' (d)　　　　　　FIG-15" (d)

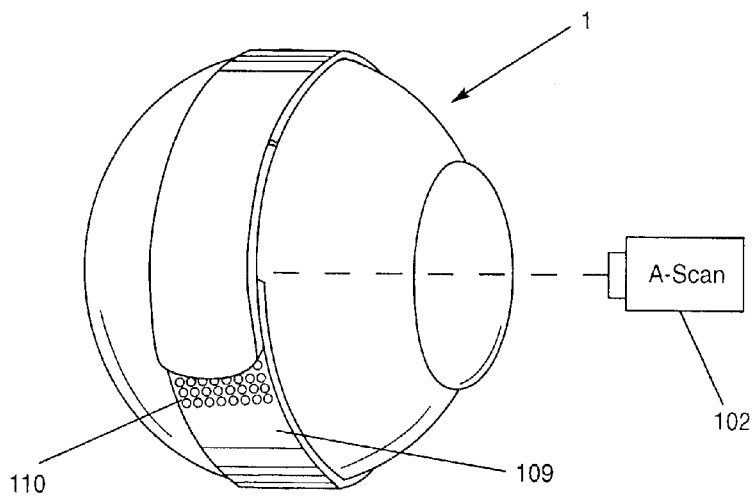
FIG-15 (e)
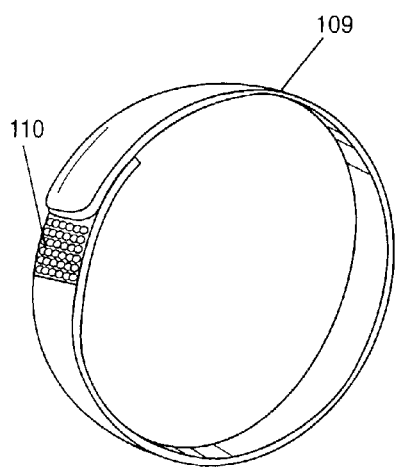
FIG-15' (e)
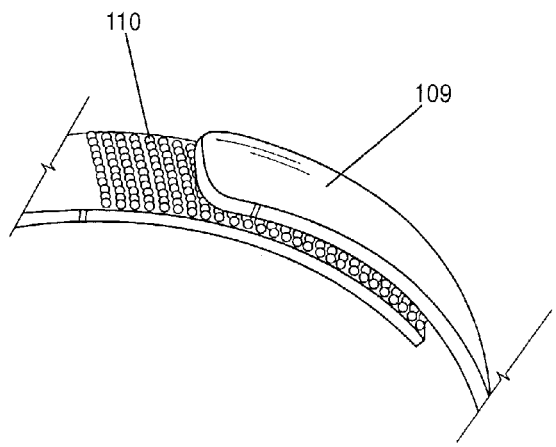
FIG-15" (e)

SURGICAL CORRECTION OF HUMAN EYE REFRACTIVE ERRORS BY ACTIVE COMPOSITE ARTIFICIAL MUSCLE IMPLANTS

CROSS-REFERENCE TO RELATED APPLICATIONS

This application is a continuation-in-part application of U.S. patent application Ser. No. 09/633,023, entitled "Surgical Correction of Human Eye Refractive Errors by Active Composite Artificial Muscle Implants", filed on Aug. 4, 2000, now U.S. Pat. No. 6,511,508, the teachings of which are incorporated herein by reference.

BACKGROUND OF THE INVENTION

1. Field of the Invention (Technical Field)

The invention relates to surgical correction of human eye refractive errors such as presbyopia, hyperopia, myopia, and astigmatism. More particularly, it is related to surgical corrections of such errors with implantation of a prosthesis for increasing or decreasing the eye length and scleral, as well a corneal, curvatures, and thus bringing the retina/macula region to coincide with the focal point of the eye. The present invention also relates to a signal energized smart prostheses equipped with composite artificial muscles for automatic correction of presbyopia. This invention can also be applicable to any medical problem requiring controlled compression and/or dilation of an internal or external mammalian organ.

2. Background Art

There are many refractive errors associated with the human eye. When the focal point of images is formed in front of the retina/macula region due to too much refraction of light rays, the refractive error is called myopia or nearsightedness. When, on the other hand, the focal point of images lies outside the eye behind the retina/macula region due to too little refraction of light rays, the refractive error is called either hyperopia or far-sightedness or presbyopia. These problems can be surgically corrected by either changing the eye length or scleral/corneal curvatures. In the case of presbyopia, as individuals age, the human eye loses its ability to focus on nearby objects. This condition, known as presbyopia, is due to a progressive loss in the elasticity of the lens of the eye. The ciliary muscles which normally force the lens, through the action of zonule fibers on the lens capsule, which is in a rounded shape, to accommodate near objects, can no longer exert the necessary changes in the lens' shape.

The conventional optometric solution to the problems of myopia, hyperopia, and presbyopia is a prescription of glasses or reading glasses; or, for individuals who already require glasses to correct other refractive errors such as myopia or astigmatism, a prescription of bifocal or multifocal glasses.

This century has witnessed a revolution in the surgical treatment of ophthalmic disorders and refractive errors of the human eye. This revolution ranges from corneal implantations, cataract extraction, phacoemulsification of the lens, intraocular lens implantation, glaucoma implants to control the intraocular pressure, radial keratotomy, excimer laser ablation of the cornea, trabeculoplasty, iridotomy, virectomy and the surgical buckle treatment of retinal detachment. The recent surgical solutions to myopia, hyperopia and astigmatism have been laser photorefractive keratectomy (PRK), Lasik (laser-assisted in-situ keratomileusis) and RK or radial keratotomy. Modern techniques proposed to correct human eye refractive errors have been corneal implants (Intacs, Keravision rings, Silvestrini, intrastromal corneal ring (ICR)) and scleral implants (SASI, Prebycorp implants, Schachar Accommodative Scleral Implants).

The effective focal length of the human eye must be adjusted to keep the image of the object focused as sharply as possible on the retina/macula. This change in effective focal length is known as accommodation and is accomplished in the eye by varying the shape of the crystalline lens. This is necessary for the human eye to have clear vision of objects at different distances. Generally speaking, in the unaccommodated normal vision, the curvature of the lens is such that distant objects are sharply imaged on the retina/macula. In the unaccommodated eye, close objects are not sharply focused on the retina/macula and their images lie behind the retinal surface. In order to visualize a near object clearly, the curvature of the crystalline lens is increased, thereby increasing its refractive power and causing the image of the near object to fall on the retina/macula. The change in shape of the crystalline lens is accomplished by the action of ciliary muscles by which the radial tension in the lens is reduced, according to classical Helmholtz theory of accommodation, and it becomes more convex. Based on the Helmholtz theory, in the unaccommodated human eye the lens and its capsule are suspended on the optical axis behind the pupil by a circular assembly of very many radially directed collagenous fibers, called zonules. These are attached at their inner ends to the lens capsule and at their outer ends to the ciliary body, a muscular constricting ring of tissue located just within the outer supporting structure of the eye, is called the sclera. The ciliary muscle is relaxed in the unaccommodated eye and therefore assumes its largest diameter. According to the Helmholtz classical theory of accommodation, the relatively large diameter of the ciliary body in this unaccommodated condition causes a tension on the zonules which in turn pull radially outward on the lens capsule, making it less convex. In this state the refractive power of the lens is relatively low and the eye is focused for clear vision of distant objects. When the eye is intended to be focused on a near object, the muscles of the ciliary body contract. This contraction causes the ciliary body to move forward and inward, thereby relaxing the outward pull of the zonules on the equator of the lens capsule and reducing the zonular tension on the lens. This allows the elastic capsule of the lens to contract causing an increase in the sphericity of the lens, resulting in an increase in the optical refraction power of the lens. Recently, Schachar (whose inventions are discussed later in this patent) has proposed a radically different theory of accommodation which refutes the Helmholtz theory.

Accordingly, the present invention relates to systems and methods of compensating presbyopia, hyperopia, myopia, and astigmatism by actively changing the length of the eye globe in the direction of optical axis or its corneal curvature, on demand, using active constricting (sphinctering) artificial muscles as active scleral bands. The scleral band in the form of an active and smart constricting/expanding band is in the form of an active prosthesis which can be remotely inductively powered by small inductive generators that can be placed near the eye, preferably behind the ears or under the skin on the shoulder or on an arm band. The scleral bands may also be inherently active due to their elasticity or resilience or due to surgically induced initial tension or compression associated with them.

The present invention can also be applicable to any medical problem requiring controlled compression and/or dilation of an internal or external mammalian organ.

There are several prior art devices and methods in the form of implants and prostheses for the surgical correction of presbyopia, hyperopia, and myopia.

SUMMARY OF THE INVENTION
(DISCLOSURE OF THE INVENTION)

The invention disclosed is an apparatus and method to create either an automatic or on-demand correction of refractory errors in the eye by the use of an active and smart (computer-controllable) scleral band equipped with composite artificial muscles. The scleral band induces scleral constriction or expansion, similar to a scleral buckle in retinal detachment surgical correction. The scleral band is preferably made from a bio-compatible material, such as silicon and comprises an encircling band around the middle of the eye's globe to provide relief of intraretinal tractional forces, for retinal detachments or buckle surgery, by indentation of the sclera as well as reposition of the retina and choroid. It can also induce myopia, depending on how much tension is placed on the buckle, by increasing the length of the eye globe in the direction of optical axis. By using the encircling scleral band, even in the absence of retinal detachment, one can actively change the axial length of the scleral globe in order to induce refractive error correction. For example, inducing a slight degree of myopia, such as one to three diopters, enables presbyopes to read without the use of glasses.

The present invention creates either active segments to be sutured to sclera or an active smart band to encircle the sclera, which constricts or expands in such a way to induce temporary myopia or hyperopia. The active artificial muscle segments can be segmentally sutured to the sclera, preferably parallel to the long axis of the eye or at some angle to create, upon activation (tension or contraction) local tension or compression on the sclera to correct axial length and scleral/corneal curvature. The smart band is implanted under the conjunctiva, preferably under the extraocular muscles. This band is secured to the sclera in a similar manner used in scleral buckle surgery. The smart band is either a singular or composite contractile artificial muscle. The muscles are either already activated by inherent pre-elasticity and pre-tension or compression induced in it after the surgical implantation or will be transcutaneously inductively powered. This produces a smart muscle band which resiliently contracts and/or expands, preferably up to 6% or more. This creates a mild scleral constriction and/or expansion which will in turn cause the length of the eye to increase and/or decrease. Thus, the retina/macula region moves to coincide with the focal point of the image of a near and/or far object. To accommodate presbyopia, hyperopia and/or myopia, the present invention induces a temporary mild myopia and/or hyperopia, thus correcting the presbyopic, hyperopic and/or myopic vision. The scleral band preferably comprises an interior body of contractile and/or expansive Shape-Memory Alloy (SMA), such as Nitinol (NiTi) or Magnetic Shape-Memory (MSM), such as NiMnGa or Ni2MnGa, and an actuator preferably in the form of wires or ribbons with attachable ends to make an endless band encased or embedded inside a silicone rubber sheath or cladding. The rubber cladding acts as a resilient structure to store potential energy when the SMA or MSM wires or ribbons contract and/or expand and use the stored resilient (springy) potential energy to stretch the contractile wires or ribbons back to their initial relaxed length. This also helps relax the sclera back to its initial dimensions. The SMA or MSM wires or ribbons go through a solid Martensite-Austenite phase transformation during their contraction, i.e., as they are transcutaneously inductively energized (MSM) or heated (SMA), at the critical Austenite start magnetic field (MSM) or temperature (SMA). The inductive generators (battery-operated magneto-resonant coils) can be housed behind the ears of the person wearing the scleral prosthesis, worn like an arm band or surgically implanted under the skin in an easily accessible location and preferably can be tuned on or off by the person wearing them by a touch of a finger (on-demand virtual reading glasses).

Other alternative embodiments are scleral constricting bands equipped with other types of composite artificial muscles such as resilient composite shape memory alloy-silicone rubber implants in the form of endless active scleral bands, electroactive ionic polymeric artificial muscle structures, electrochemically contractile endless bands of ionic polymers such as polyacrylonitrile PAN, thermally contractile liquid crystal elastomer artificial muscle structures, magnetically deployable structures or other deployable structures equipped with smart materials such as piezocerams, piezopolymers, electroactive and electrostrictive polymers, magnetostrictive materials, magnetic shape memory materials and electro or magnetorheological materials.

Another alternative embodiments comprise smart active bands that are energized by means of a voltage signal generated by a small piece of ionic polymeric artificial muscle acting as a deformation sensor and sutured to the ciliary muscle. When the ciliary muscle contracts in near vision situations (the eyes converge to view the near object), the sutured ionic polymeric artificial muscle generates a voltage signal of a few millivolts which in turn can trigger a switch or can be amplified to activate the implanted smart scleral band. This embodiment creates an automatic and on-demand accommodation for near vision situations and presbyopia.

To install the scleral band the following surgical procedure is performed. A 360-degree conjunctiva peritomy is performed. The conjunctiva is carefully dissected free from the sclera. Each of the extraocular muscles are isolated and freed form the check ligaments. The composite artificial muscle band is then placed underneath the extraocular muscles and then secured together creating a 360 degree band encircling the sclera. The band tension is adjusted in order to achieve emmetropia using an A-scan (ultrasonic determination of eye length and correct vision). The band is then secured to the sclera using a locking mechanism as well as 6.0 nylon sutures, or the like. In the alternative, the artificial muscle band can be placed 3 mm from the sclera and the band implanted one half thickness into the sclera. The simplest method of implantation is similar to the method used for scleral buckle surgery. The two alternative positions will increase the axial length of the globe. The active composite artificial muscle will deactivate on command returning the axial length to its original position and vision back to normal (emmetropic vision).

A primary object of the present invention is to create on-demand correction of refractory errors in the eye by the use of an active and smart (computer-controllable) scleral band or segments or ribs equipped with composite artificial muscles.

Another object of the present invention is to create active segments or ribs or an active smart band to encircle the sclera, which will constrict or expand in such a way to induce temporary myopia or hyperopia.

Yet another object of the present invention to provide a device and method for focusing the eyes at a near point wherein the focusing activity is automatically stimulated by the natural contraction of the ciliary muscle when viewing a close object and returning to the natural state when the ciliary muscle is relaxed.

A primary advantage of the present invention is that the installation of the present invention on a human eye does not include destructive intervention like the present implantable devices or laser correctional surgery such as RK, PRK or Lasik.

Another advantage of the present invention is that this will be an active and smart mechanism to be implemented when one is reading. In the case of inherently active (pretensioned but otherwise passive) band correcting presbyopia, only a single band will be surgically implanted on the non-dominant eye of a person.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 3(a) shows another rendition of FIG. 2(a) in an open configuration;

FIG. 3(b) shows another rendition of FIG. 2(b) in an open configuration;

FIG. 4(a) shows the invention of FIG. 1 around the outside surface of the sclera sutured and fixated under the extraocular muscles of the eye in a relaxed inactivated state;

FIG. 4(b) shows the invention of FIG. 4(a) in an activated state causing the sclera to buckle and the eye length to increase;

FIG. 5(a) is an isometric view of an alternate embodiment of the invention equipped with electroactive ionic polymeric sensors and actuator active bi-strip loops;

FIG. 5(b) is a front view of the embodiment of FIG. 5(a);

FIG. 5(c) shows the ionic polymer active by-strips of FIG. 5(a) with induction coils;

FIG. 8(a) is an isometric view of another alternate embodiment of the invention equipped with an inextensible support band and an inflatable bladder skirt for pneumatically squeezing or expanding the scleral globe by means of a blow/suction tube in the individual's nose to induce lengthening of the globe;

FIG. 8(b) shows the embodiment of FIG. 8(a) attached to a users nose;

FIG. 9(a) depicts another embodiment of the present invention in which the constricting action is obtained by an endless solenoid or coil gun configuration composed of a telescopically constricting tubular band with a golden armature winding and a gold-plated hollow projectile in an expanded configuration;

FIG. 9(b) depicts another embodiment of the present invention in which the constricting action is obtained by an endless solenoid or coil gun configuration composed of a telescopically constricting tubular band with a golden armature winding and a gold-plated hollow projectile in a constricting configuration;

FIG. 10(a) shows a side view of another embodiment of the active scleral band of this invention wherein the band is comprised of a bio-compatible resilient polymer;

FIG. 10(b) shows an isometric view of FIG. 10(a) and yet another embodiment of the active scleral band of this invention wherein the band is comprised of a bio-compatible resilient polymer;

FIG. 11(a) shows an isometric view of another embodiment of the invention in initial stage of operation as a scleral expansion band to shorten the eye length to correct myopia;

FIG. 11(b) shows an isometric view of FIG. 11(a) in an active expanded configuration;

FIG. 11(c) shows a side view of the embodiment of FIG. 11(b);

FIG. 15(a) depicts an alternative embodiment of an inherently active band with a foot-heel type tensioning and locking mechanism;

FIG. 15(b) depicts an alternative embodiment of an inherently active band with a buckle-type tensioning and locking mechanism placed around the sclera;

FIG. 15'(b) depicts an alternative embodiment of an inherently active band with a buckle-type tensioning and locking mechanism;

FIG. 15"(b) depicts a close-up of an alternative embodiment of an inherently active band with a buckle-type tensioning and locking mechanism;

FIG. 15(c) depicts an alternative embodiment of an inherently active band with a adjustable screw-type or bolt and nut type tensioning and locking mechanism;

FIG. 15'(c) depicts an alternative embodiment of an inherently active band with a adjustable screw-type or bolt and nut type tensioning and locking mechanism;

FIG. 15"(c) depicts a close-up an alternative embodiment of an inherently active band with a adjustable screw-type or bolt and nut type tensioning and locking mechanism;

FIG. 15(d) depicts an alternative embodiment of an inherently active band with a peg-in-hole type tensioning and locking mechanism placed around the eye ball;

FIG. 15'(d) depicts an alternative embodiment of an inherently active band with a peg-in-hole type tensioning and locking mechanism;

FIG. 15"(d) depicts a close-up of an alternative embodiment of an inherently active band with a peg-in-hole type tensioning and locking mechanism;

FIG. 15(e) depicts an alternative embodiment of an inherently active band with a Velcro® type tensioning and locking mechanism placed around the eye ball;

FIG. 15'(e) depicts an alternative embodiment of an inherently active band with a Velcro® type tensioning and locking mechanism;

FIG. 15"(e) depicts a close-up of an alternative embodiment of an inherently active band with a Velcro® type tensioning and locking mechanism;

FIG. 15(f) depicts an alternative embodiment of an inherently active band with multiple-pin ratchet-type tensioning and locking mechanism placed around the eye ball;

FIG. 15'(f) depicts an alternative embodiment of an inherently active band with a saw tooth ratchet-type tensioning and locking mechanism;

FIG. 15"(f) depicts a close-up of an alternative embodiment of an inherently active band with a saw tooth ratchet-type tensioning and locking mechanism;

Figure 1A:
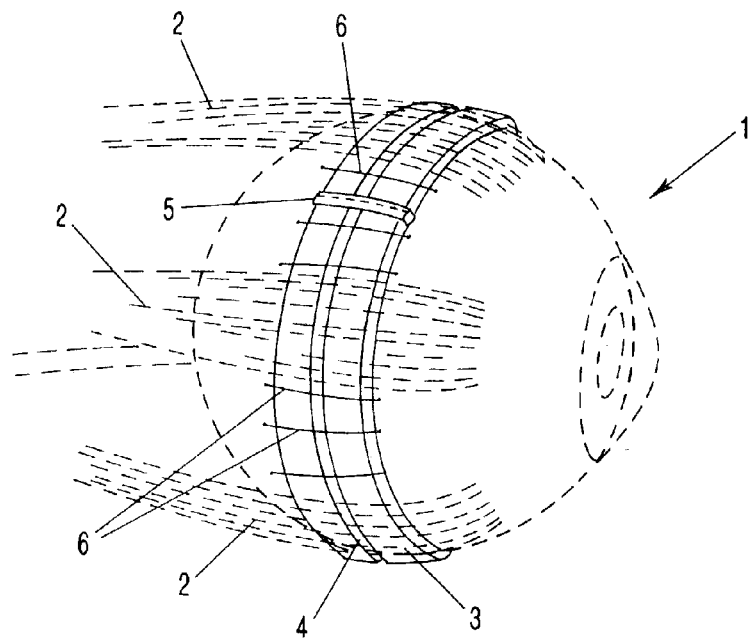
FIG. 1(a) is an isometric view of the present invention surgically mounted on the scleral globe under the extraocular muscles and sutured to the anterior surface of the sclera.
Figure 1B:
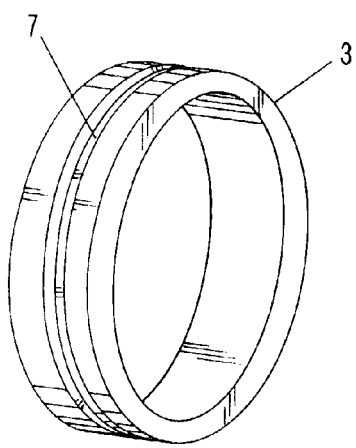
FIG. 1(b) is a scleral buckle tire with an annular groove used to create a cushion between the active scleral constricting band placed in the annular groove of the tire and the scleral anterior surface.
Figure 1C:
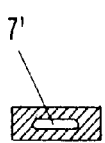
FIG. 1(c) is a scleral buckle tire with an annular tunnel used to create a cushion between the active scleral constricting band placed in the annular tunnel of the tire and the scleral anterior surface.
Figure 1D:
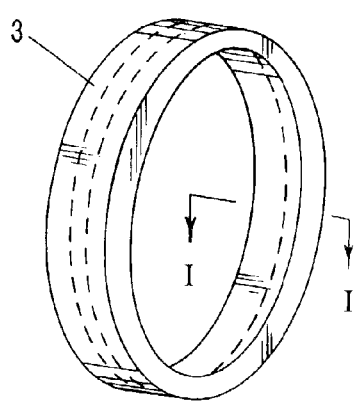
FIG. 1(d) is a cut out view of FIG. 1(c) showing the configuration of the tire and the active scleral constrictive band placed in the groove of the tire.
Figure 1E:
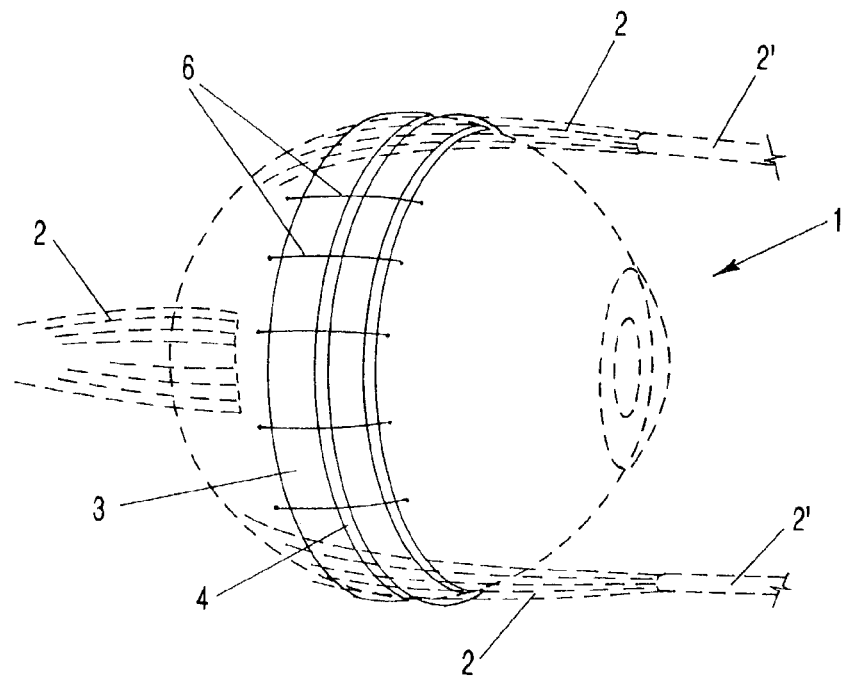
FIG. 1(e) is a cut out view of FIG. 1(a) showing the configuration of the tire and the active scleral constrictive band placed in the groove, as shown in FIG. 1(b) of the tire.
Figure 1F:
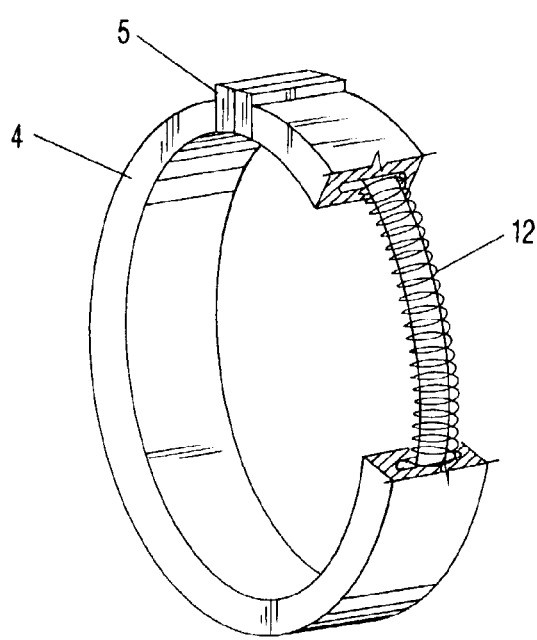
FIG. 1(f) is a transparent rendition of the active scleral constrictive band composed of embedded artificial muscle wire induction coil assembly, embedded inside a silicone rubber cladding with snappable ends.

DESCRIPTION OF THE PREFERRED EMBODIMENTS (BEST MODES FOR CARRYING OUT THE INVENTION)

This invention creates automatic (passive) or on-demand temporary change in eye length and corneal/scleral curvatures by the use of band assembly that constricts and/or expands either inherently or on demand. The invention employs composites artificial muscles in an implant or prosthesis to surgically correct presbyopia, hyperopia and myopia, on demand (virtual reading glasses). For example, this invention can induce temporary mild myopia, one to three diopters, which has been shown to enable presbyopes to read without the use of glasses in order to correct presbyopia, hyperopia, and myopia. The invention creates an active sphinctering smart band to encircle the sclera, implanted under the conjunctiva, preferably under the extraocular muscles which will expand or constrict, similar to a scleral buckle surgery. This increases or decreases the active length of the globe and changes the curvature of the cornea and thus corrects presbyopia, hyperopia, and myopia either automatically or on demand.

FIGS. 1 (a, b c, d, e and f) show an isometric view of the composite scleral tire or band 3 and composite artificial muscle active scleral band 4 surgically mounted on the scleral globe or eye 1 under the extraocular muscles 2 and mattress sutured 6 to the anterior surface of the sclera 10. Artificial muscle assembly 12 is embedded inside silicone cladding 4 with the snappable ends 5 to be placed inside the groove 7 or the tunnel 7' of scleral tire 3. The surgical procedure is such that the artificial muscle assembly 12 embedded inside silicone cladding 4 in the form of a band will be placed inside the central groove 7 or tunnel 7' of the scleral tire 3 in a relaxed and stress free state. The scleral tire assembly or smart band 3 is then surgically placed equatorially around the sclera similar to scleral buckle surgery and mattress sutured 6 to the sclera globe 1.

The operation of the smart band 3 is such that upon transcutaneous inductive energizing electromagnetically or by heating of the endless artificial assembly to shrink or expand, such as in magnetic shape memory materials (MSM) or shape memory alloys (SMA), the inductive coil assembly 12, embedded inside the silicone cladding 4 and placed in the scleral tire assembly 3, for the artificial muscle activation, the smart band will either contract or expand to correct refractive errors by changing the eye length as well as corneal scleral curvatures.

Figure 2A:
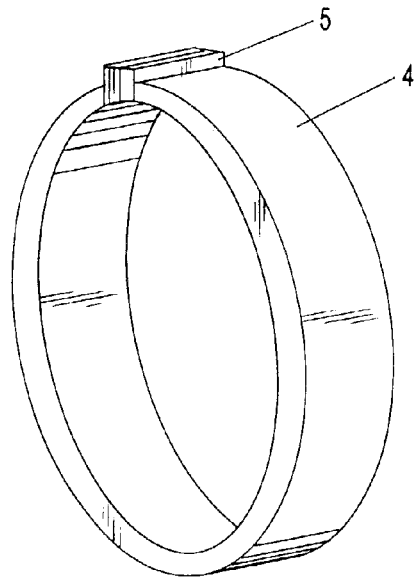
FIG. 2(a) shows an exploded view of the invention of FIG. 1 with silicone cladding.
Figure 2B:
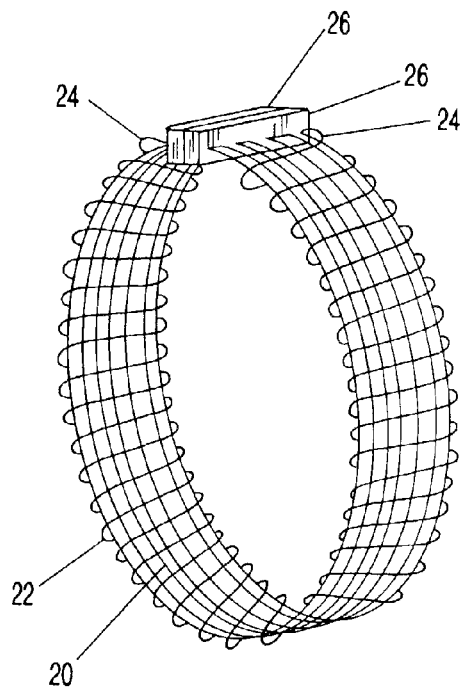
FIG. 2(b) is another exploded view of FIG. 1 showing the embedded SMA wires (ribbons) and the induction coil wrapped around the SMA wires (ribbons)
Figure 2C:
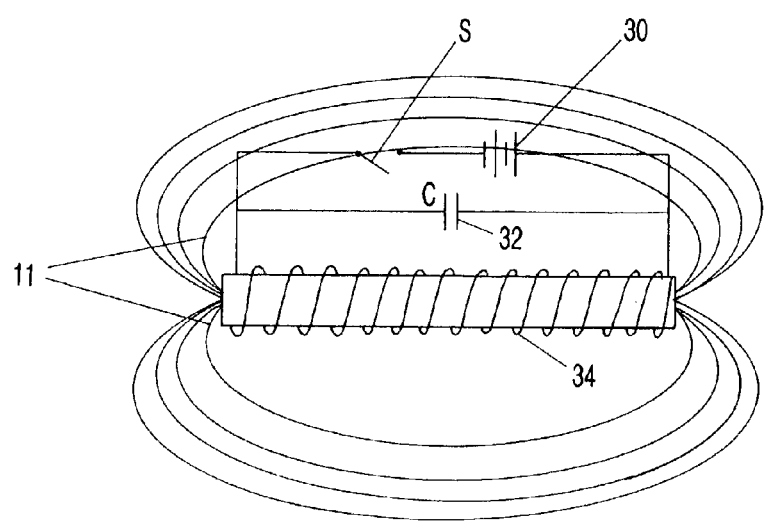
FIG. 2(c) shows the induction generator powered by a source and stabilized by a capacitor creating the induction flux lines to induce a current in the induction coil of FIG. 2(b)

FIGS. 2(*a*), 2(*b*), and 2(*c*) show an exploded view the composite MSM or SMA-silicone artificial muscle active scleral band 12 of FIG. 1. FIG. 2(*a*) shows a scleral band 12 with silicone cladding 4 and tension adjustable and lockable or snappable ends 5. FIG. 2(*b*) shows the embedded MSM or SMA wires or ribbons 20 and the induction coil 22 wrapped around the SMA wires 20. The ends of the SMA wires 24 are connected to end fixtures 26 by bonding or other well known affixing means. End fixtures 26 can snap or bond together by standard means such as sutures, magnets, Velcro®, or the like. FIG. 2(*c*) shows the induction generator 34 powered by a battery source E 30 and stabilized by a capacitor C 32, thereby creating the induction flux lines 11 to induce a current in the induction coil 22 of FIG. 2(*b*). Thus, one can remotely energize, by magnetic means, the MSM wires 20 or heat the SMA wires 20 to an Austenite start magnetic field or temperature.

FIG. 3 shows another rendition of FIGS. 2(*a*) and 2(*b*) in an open configuration. Silicone cladding 4 houses the MSM or SMA wires 20 which are wrapped by means of an induction coil 22. The MSM or SMA wires 20 are attached to end fixtures 26 with holes through which the wires 20 are serpentined and zigzagged and eventually connected to pins 8' and 9' by means of end connector wires 8 and 9. The assembly of MSM or SMA wires 20 and end fixtures 26 and induction coil 22 are embedded in the silicone cladding 4 which are attached to end fixtures 26. End fixtures 26 can have snappable ends 5 which may preferably snap or bond together by standard means such as belt buckles, snaps, ratchets, screws, sutures, magnets, Velcro®, or the like.

FIG. 4(*a*) shows the composite scleral tire 3 with a MSM-Silicone or SMA-silicone artificial muscle active scleral band 3 of FIG. 1, around the outside surface of the sclera 10 of the eye in a relaxed inactivated state. FIG. 4(*b*) shows the invention in an activated state causing the sclera 10 to buckle or constrict and the eye length and corneal curvature to increase.

FIGS. 5(*a*), 5(*b*), and 5(*c*) show another embodiment of the invention equipped with electroactive ionic polymeric sensors and actuator bi-strips 40. FIG. 5(*b*) is a front view of the eye globe with sclera 10, bi-strip actuators 40 and an inextensible support band 42. FIG. 5(*c*) shows the ionic polymer active bi-strips equipped with an active polymer 44, induction coil 46, and end electrodes 48. Upon transcutaneous inductive powering of the bi-strip polymeric artificial muscle actuators 40, embedded inside the smart band 3, the bi-strips 44 expand outward and exert a constricting or squeezing circularly distributed force or pressure on the scleral tire 3 which in turn transmits that distributed annular force to the sclera 10, causing the axial length and local curvature of eye 1 to increase. This will bring the retina/ macula region to coincide with the focal point of the eye and thus correct presbyopia.

Figures 6A, 6B:
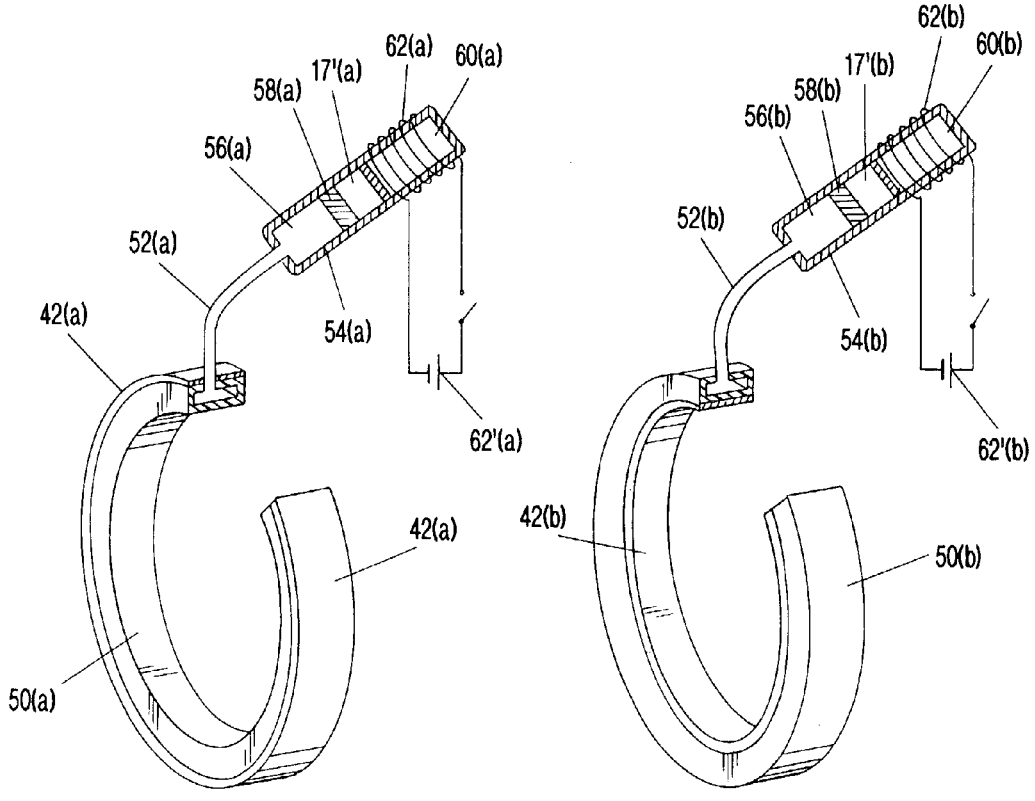
FIG. 6(a) is an isometric view of another alternate embodiment of the invention equipped with an inextensible outer support band and an inflatable inner bladder skirt for pneumatically squeezing the scleral globe to induce lengthening of the globe to correct hyperopia or presbyopia.
FIG. 6(b) is an isometric view of another alternate embodiment of the invention equipped with an inextensible inner support band and an inflatable outer bladder skirt for pneumatically expanding the scleral globe to induce shortening of the globe to correct myopia.

FIG. 6(*a*) shows an isometric view of yet another embodiment of the invention. In this embodiment hydrogen gas is absorbed and desorbed using metal hydrides to cause a tightening and releasing of a band affixed to the scleral globe. The method for using metal hydrides in this fashion is described in Y. Wakisaka, et. al., Application of Hydrogen Absorbing Alloys to Medical & Rehabilitation Equipment, IEEE Trans. on Rehabilitation Engineering, Vol. 5, No. 2, pp. 148–157, (1997). This embodiment comprises an inextensible outer support band 42(*a*) and an inflatable bladder skirt 50(*a*) for pneumatically squeezing the scleral globe 1 to induce lengthening of the globe. The inflation of the bladder 50(*a*) is created by a tube 52(*a*) attached to a cylinder 54(*a*) containing a source of bio-compatible gas, such as $CO_2$ or the like, in reservoir 56(*a*) to be pressurized by a piston 58(*a*) by means of a hydrogen gas 17'(*a*), which is desorbed from a metal hydride reservoir 60(*a*). The metal hydride reservoir 60(*a*) is transcutaneously and remotely inductively heated by an induction coil 62(*a*) to cause hydrogen to desorb from it and push piston 58(*a*) to pressurize inner bladder 50(*a*) by the $CO_2$ gas in reservoir 60(*a*). The inflation of inner bladder 50(*a*) against the inextensible outer support band 42(*a*), uniformly and circularly constricts the scleral tire 3 which in turn causes the eye length to increase and thus, correct presbyopia and hyperopia by bringing the retina/macula region to coincide with the focal point of the eye.

FIG. 6(*b*) shows an isometric view of yet another embodiment of the invention similar to FIG. 6(*a*). In this embodiment hydrogen gas is absorbed and desorbed using metal hydrides to cause a tightening and releasing of a band affixed to the scleral globe 1. This embodiment comprises an inextensible inner support band 42(*b*) and an inflatable outer bladder skirt 50(*b*) for pneumatically expanding the scleral globe 1 to induce shortening of the globe. The inflation of the bladder 50(*b*) is created by a tube 52(*b*) attached to a cylinder 54(*b*) containing a source of bio-compatible gas, such as $CO_2$ or the like, in reservoir 56(*b*) to be pressurized by a piston 58(*b*) by means of a hydrogen gas 17'(*b*) which is desorbed from a metal hydride reservoir 60(*b*). The metal hydride reservoir 60(*b*) is transcutaneously and remotely inductively heated by an induction coil 62(*b*) or a battery 62'(*a*) to cause hydrogen to desorb from it and push piston 58(*b*) to pressurize outer bladder 50(*b*) by the $CO_2$ gas in reservoir 60(*b*). The inflation of outer bladder 50(*b*) against the inextensible inner support band 42(*b*), uniformly and circularly expands the scleral tire 3 which in turn causes the eye length and corneal curvature to decrease and thus correct myopia by bringing the retina/macula region to coincide with the focal point of the eye.

Figure 7A:
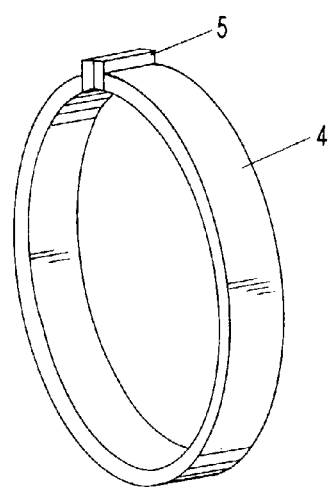
FIG. 7(a) is an isometric view of yet another alternate embodiment of the invention equipped with contractile electrically actuated polymeric or liquid crystal elastomeric fibers enclosed inside a silicone rubber cladding.
Figure 7B:
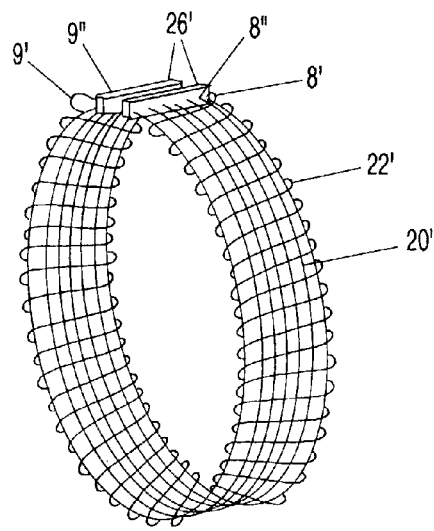
FIG. 7(b) is an isometric view of the liquid crystal elastomer wires enclosed inside an inductive heating coil similar to FIG. 2(b)

FIGS. 7(*a*) and 7(*b*) show another embodiment of the invention equipped with contractile electrically actuated polymeric or liquid crystal elastomeric fibers. FIG. 7(*a*) shows the prosthesis with silicone cladding 4 and snappable ends 5. FIG. 7(*b*) shows the embedded contractile liquid crystal elastomer (LCE) wires or ribbons 20' and the induction coil 22' wrapped around the LCE wires. FIG. 7(*b*) also depicts the ends of the LCE wires 8' and 9' and their point of connections to the LCE wire assembly 8" and 9" and the end fixtures 26' to which the LCE wires are bonded. End fixtures 26' can be snapped or bonded together by standard means such as sutures, belt buckles, snaps, ratchets, screws, magnets, Velcro®, or the like. Referring to FIG. 2(*c*), note that the induction generator 34, powered by a battery source E 30 and stabilized by a capacitor C 32 creates the induction flux lines 11 to induce a current in the induction coil 22' of FIG. 7(*b*). Thus, one can remotely energize the LCE wires to a an isotropic-nematic phase transition temperature of about 40 degrees Celsius to cause the wires to contract and thus causing the prosthesis to uniformly and circularly constrict the sclera to cause an increase in the eye length and thus correct presbyopia and accommodate near object vision.

FIGS. 8(*a*) and 8(*b*) show an embodiment of the invention equipped with an inextensible support band 3 with snappable end fixtures 5 and an inflatable bladder skirt 50. The operation of the device is such that one pneumatically squeezes the scleral globe by means of a blow/suction tube 64 with a wider inlet 66 surgically implanted in the individual's nostrils as shown in FIG. (8*b*) to induce lengthening or shortening of the eye globe by means of the exhaled/inhaled $CO_2$ gas from the lungs.

FIGS. 9(*a*), 9(*b*), and 9(*c*) depict another embodiment of the present invention in which the constricting action is obtained by an endless solenoid or coil gun configuration composed of a telescopically constricting tubular band 70 with a golden armature winding 72 and a gold-plated hollow projectile 74. The operation of this embodiment, which will be placed in the groove or the tunnel of the scleral tire already described, is such that upon transcutaneous inductive powering of the electromagnetic coil 72 the gold-plated projectile 74 will move in a direction to constrict the band and make its inner diameter smaller. Thus constricting or expanding effects are obtained to lengthen or shorten the eye and correct presbyopia, hyperopia or myopia on demand. FIG. 9(*a*) depicts an expanded configuration of the endless solenoid assembly, while FIG. 9(*b*) depicts a constricted configuration of the endless solenoid assembly. The solenoid assembly is powered by an inductive generator (not shown).

FIG. 10(*a*) shows a side view of another embodiment of the active scleral band of this invention comprising a bio-compatible resilient polymer band 80, such as silicone with lockable male-female ends 86–88. The surgeon, in this case fixably implants the bio-compatible resilient polymer band 80 equatorially in the groove or the tunnel of the scleral tire which is already sutured to the sclera and adjusts the locking distance by choosing a certain insertion distance for the male-female locking ends 86 and 88. In doing so the surgeon pushes over the unlocking hole 82 in the transverse direction 84 to allow for easy adjustment of the locking insertion distances.

FIG. 10(*b*) shows an isometric view of FIG. 10(*a*) and yet another embodiment of the bio-compatible resilient polymer band 80 of this invention wherein the band is comprised of a bio-compatible resilient polymer such as silicone with lockable male-female ends 86–88 and unlocking hole 82. To adjust the surgeon merely pushes the ends together.

FIG. 11(*a*) shows an isometric view of yet another embodiment of the invention used for myopes in the initial stage of operation (unsutured band) as a scleral expansion band 83 over the sclera 10 and under the extraocular muscles 2 to shorten the eye length and decrease corneal curvature to correct myopia in such a way that the retina/macula region is moved to coincide with focal point of the image 14.

FIG. 11(*b*) shows an isometric view of the embodiment of FIG. 11(*a*) in the final stage of operation (mattress sutured 6) as a scleral expansion band 83 over the sclera 10 and under the extraocular muscles 2 to shorten the eye length to correct myopia in such a way that the retina/macula region is moved to coincide with focal point of the image 14. FIG. 11(*c*) shows a side view of the embodiment of FIG. 11(*b*) in the final stage of operation, showing the location of sutures 6, as a scleral expansion band 83, to shorten the eye length and decrease corneal curvature to correct myopia.

Figure 12B:
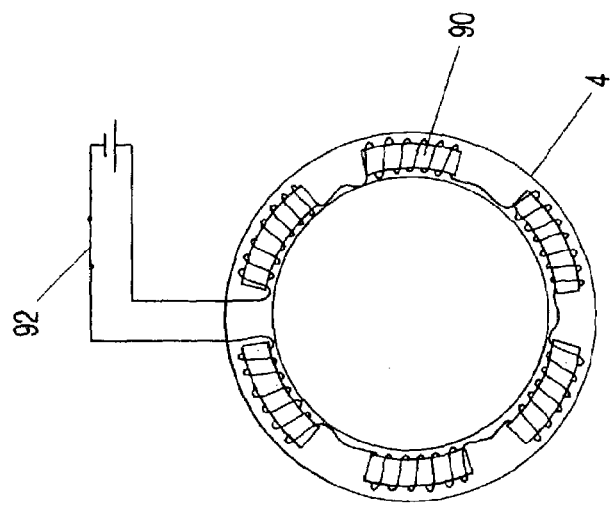
FIG. 12(b) depicts the same embodiment of FIG. 12(a) in an activated state.
Figure 12A:
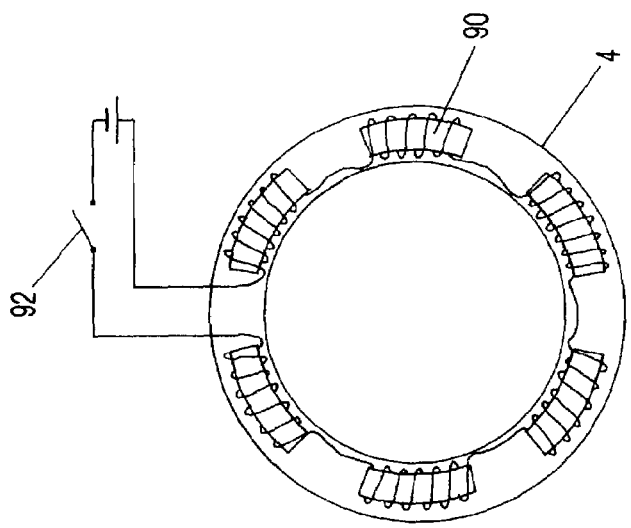
FIG. 12(a) depicts another embodiment of an active constrictive band composed of silicone rubber cladding with embedded electro magnets in an activated state.

FIG. 12(*a*) is yet another embodiment of the active scleral band made with silicone rubber cladding 4 with embedded electro magnets 90 such that upon activation by switch 92 the active band constricts as shown in FIG. 12(*b*). Electro magnets 90 upon activation, attract each other thus shortening the circumference of the silicone cladding 4. Upon deactivation, the elasticity of the silicone cladding 4 will expand the ring to its initial diameter.

Figure 13:
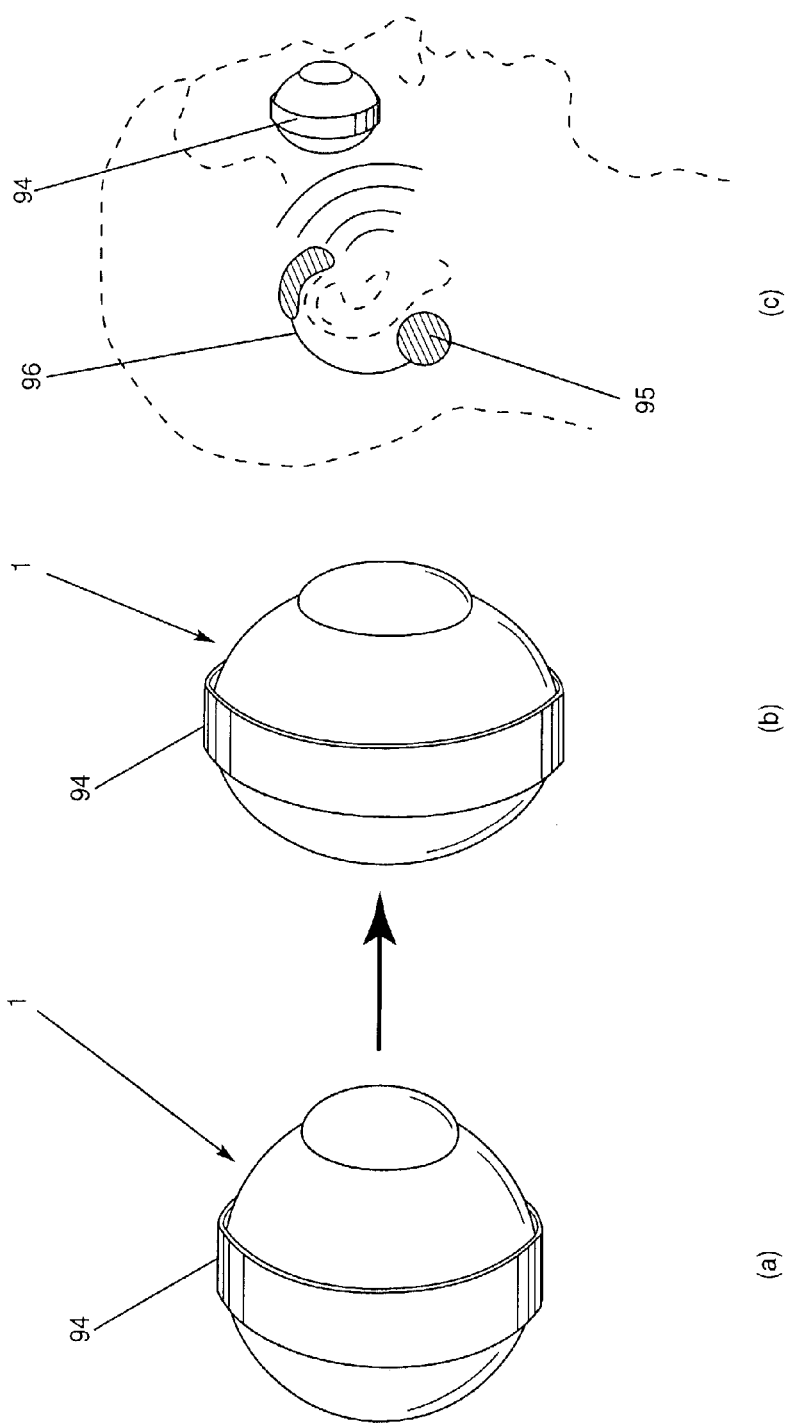
FIG. 13(a) depicts a myopic (long) eye in which the image is formed inside the eye and a scleral band made with Magnetic Shape Memory (MSM) material is in a non-activated state.
FIG. 13(b) depicts the same myopic eye as in FIG. 13(a) being corrected to an emmetropic eye (normal vision) by the expansion of MSM scleral band due to inductive powering by an external magnetic field.
FIG. 13(c) depicts the inductive powering operation of an inductive generator behind the ear of the user, like a hearing aid, to activate the magnetic shape memory band around the sclera.

FIG. 13(*a*) depicts yet another embodiment of a myopic or long eye in which the image is formed inside the eye 1 and a magnetic shape memory (MSM) artificial muscle scleral band 94 in a non-activated state. FIG. 13(*b*) depicts the same myopic eye 1 as in FIG. 13(*a*) being corrected to an emmetropic eye or normal vision by the expansion of the MSM artificial muscle scleral band 94 due to inductive powering by an external magnetic field. FIG. 13(*c*) depicts the inductive powering operation of an inductive generator 95 behind the ear 96 of the user, like a hearing aid, to activate the MSM artificial muscle scleral band 94 around the sclera.

Figure 14:
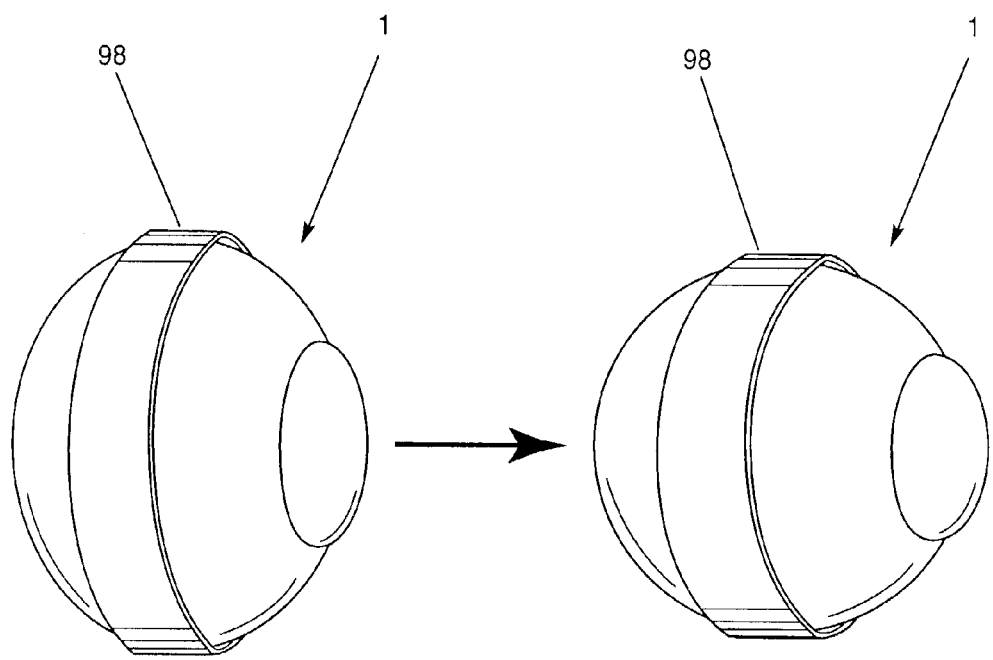
FIG. 14(a) depicts a hyperopic (short) or presbyopic eye in which the image is formed outside (behind) the eye and a scleral band made with either a Magnetic Shape Memory (MSM) material or a polymeric heat-shrink material which is in a non-activated state.
FIG. 14(b) depicts the same hyperopic or presbyopic eye as in FIG. 14(a) being corrected to an emmetropic eye (normal vision) by the constriction of MSM scleral band due to inductive powering by an external magnetic field or constriction of polymeric heat-shrink scleral band due to being heated by an external heat source.

FIG. 14(*a*) depicts yet another embodiment of a hyperopic, short or presbyopic eye 1 in which the image is formed outside or behind eye 1 and a MSM or polymeric heat-shrink artificial muscle scleral band 98 in a non-activated state. FIG. 14(*b*) depicts the same hyperopic or presbyopic eye as in FIG. 14(*a*) being corrected to an emmetropic eye or normal vision by the contraction of MSM or polymeric heat-shrink artificial muscle scleral band 98 due to inductive powering by an external magnetic field or by heating by an external heat source.

Figure 15:
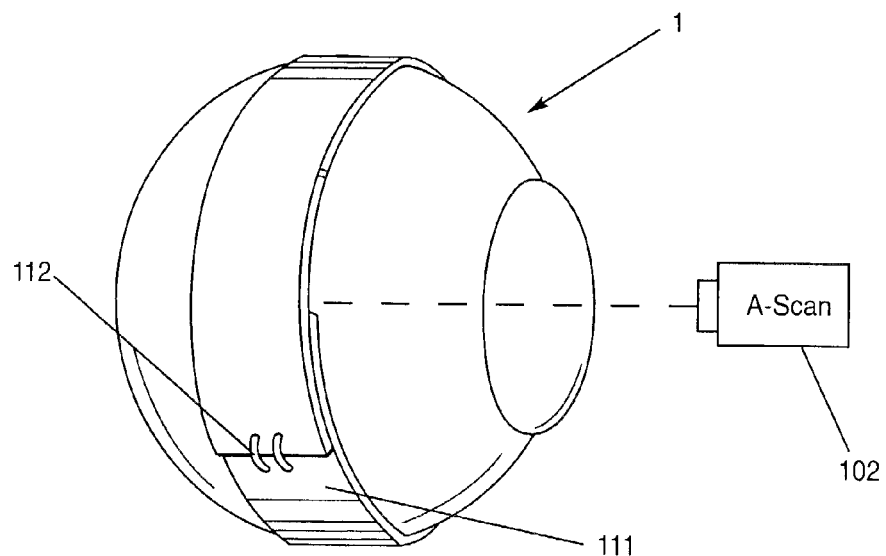
FIG. 15'(a) depicts an alternative embodiment of an inherently active band with a foot-heel type tensioning and locking mechanism in an unactivated state.
Figure 15:
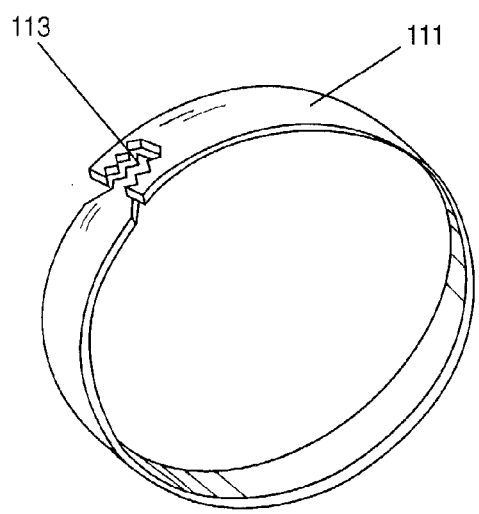
Figure 15:
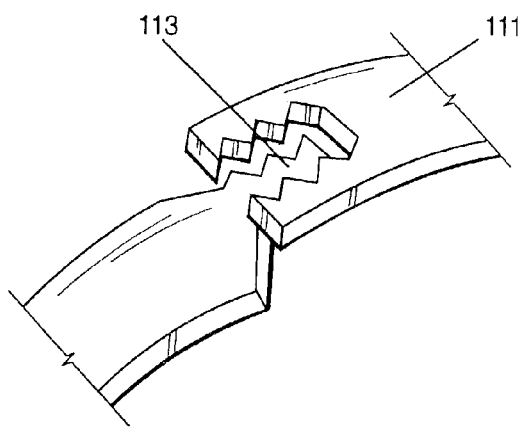

FIGS. 15(*a*), 15'(*a*), and 15"(*a*) depict alternative embodiments of an inherently active band 101 with a foot-heel type tensioning and locking mechanism 100. In this configuration, the surgeon tightens the band 101 as much as needed to create correct vision using an A-scan 102. Once the right length of the eye 1 is achieved, the surgeon, using the ultrasonic A-scan 102 then tightens the locks in place on the band 101 and completes the surgical operation by placing the conjunctiva back, and re-suturing the eye.

Note that FIGS. 15'(*a*) and 15"(*a*) depict this type of band in a non-activated and an activated configuration, respectively.

FIGS. 15(*b*), 15'(*b*), and 15"(*b*) depict another alternative embodiment of an inherently active band 103 with a buckle-type tensioning and locking mechanism 104. In this configuration, the surgeon tightens band 103 as much as needed to create correct vision using an A-scan. Once the right length of eye 1 is achieved, the surgeon, using the ultrasonic A-scan 102, tightens the locks in place on band 103 and completes the surgical operation by placing the conjunctiva back, and re-suturing the eye.

FIGS. 15(*c*), 15'(*c*), and 15"(*c*) depict another alternative embodiment of an inherently active band 105 with an adjustable screw-type or bolt and nut type tensioning and locking mechanism 106. In this configuration, the surgeon tightens band 105 as much as needed to create correct vision using an A-scan 102. Once the right length of eye 1 is achieved, the surgeon, using the ultrasonic A-scan 102, tightens the locks in place on band 105 and completes the surgical operation by placing the conjunctiva back, and re-suturing the eye.

FIGS. 15(d), 15'(d), and 15"(d) depict an alternative embodiment of an inherently active band 107 with a peg-in-hole type tensioning and locking mechanism 108. In this configuration, the surgeon tightens band 107 as much as needed to create correct vision using an A-scan. Once the right length of eye 1 is achieved, the surgeon, using the ultrasonic A-scan 102, tightens the locks in place on band 107 and completes the surgical operation by placing the conjunctiva back, and re-suturing the eye.

FIGS. 15(e), 15'(e), and 15"(e) depict an alternative embodiment of an inherently active band 109 with a hook and loop or Velcro® type tensioning and locking mechanism 110. In this configuration, the surgeon tightens band 109 as much as needed to create correct vision using an A-scan. Once the right length of eye 1 is achieved, the surgeon, using the ultrasonic A-scan 102, tightens the locks in place on band 109 and completes the surgical operation by placing the conjunctiva back, and re-suturing the eye.

FIG. 15(f) depicts an alternative embodiment of an inherently active band 111 with multiple lock-in pin ratchet-type tensioning and locking mechanism 112. In this configuration, the surgeon tightens band 111 as much as needed to create correct vision using an A-scan 102. Once the right length of eye 1 is achieved, the surgeon, using ultrasonic A-scan 102, tightens the locks in place on band 111 and completes the surgical operation by placing the conjunctiva back, and re-suturing the eye.

FIG. 15'(f) depicts another embodiment of the band 111 with saw tooth ratchet-type tensioning and locking mechanism 113.

FIG. 15"(f) is a close-up view of the band 111 and the saw tooth ratchet-type tensioning and locking mechanism 113.

Figure 16:
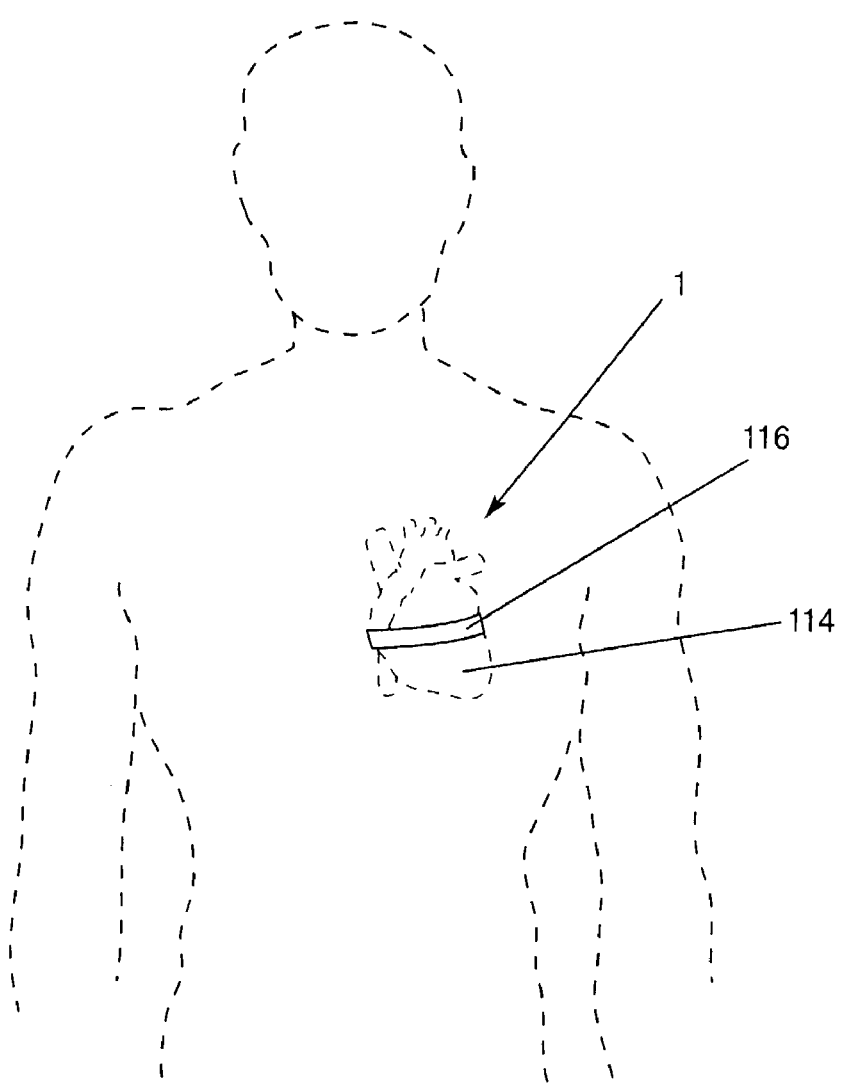
FIG. 16 depicts an internal mammalian organ being either compressed or dilated by an external band.

FIG. 16 depicts an internal mammalian organ 114 being either compressed or dilated by an external band 116 in a body 1, as described in FIGS. 1 through 15. Examples of such internal organs that may need medically administered compression and/or expansion include the stomach, the heart, the aorta, body tissues, muscles, bones, urethral passages, urinary tracks, intestines, and the like.

Figure 17:
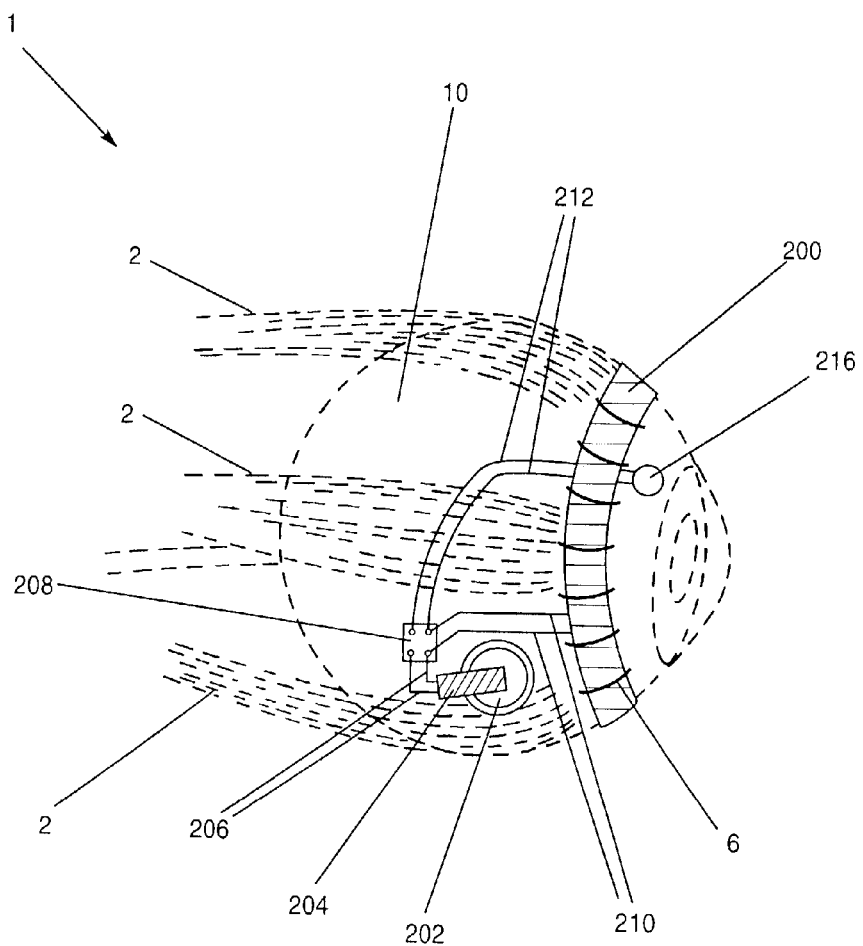
FIG. 17 is a schematic of an eye with an scleral band sutured over the ora serrata region of the eye and electrically wired to a relay and logic control unit and on/off switch and an embedded small battery which can activate the band to constrict and accommodate near vision once a signal is received by the relay and logic control unit from a sensor sutured to the ciliary muscle.

FIG. 17 shows the automatic scleral band. Eye 1 includes the extraocular muscles 2, the active scleral band 200 sutured to the sclera 10 over the ora serrata region by means of sutures 6. Artificial muscle sensor 202 is bonded to the ciliary muscle 204 and wired, by means of a first pair of wires 206, to a solid-state relay and logic control unit 208. Solid-state relay and logic control unit 208 is bonded to the sclera 10 and connected to the active scleral band 200 by means of a second pair of electrical wires 210. Small implantable and transcutaneously rechargeable battery 216 is bonded to sclera 10 and connected to the active scleral band 200 by means of the second pair of electrical wires 210 and connected to the relay and logic control unit 208 by a third pair of electrical wires 212.

The operation of this embodiment is that upon near vision accommodation, ciliary muscle 204 contracts and causes bonded artificial muscle sensor 202 to send a voltage signal of a few millivolts to the relay and logic control unit 208 by means of conducting wires 206. Solid-state relay and logic control unit 208 switches on second electrical wires 210 and third electrical wires 212, thus energizing the active scleral band by means of second electrical wires 210 and third electrical wires 212. Active scleral band 200 constricts the ora serrata region causing the eye length and corneal and lens curvatures (convexity) to increase and allow for near vision accommodation automatically. Once the ciliary muscles relax, the signal from the sensor approaches a zero value and solid-state relay and logic control unit 208 switches off battery 216 from energizing active band 200 and the band relaxes allowing the eye to return to normal vision.

Figure 18:
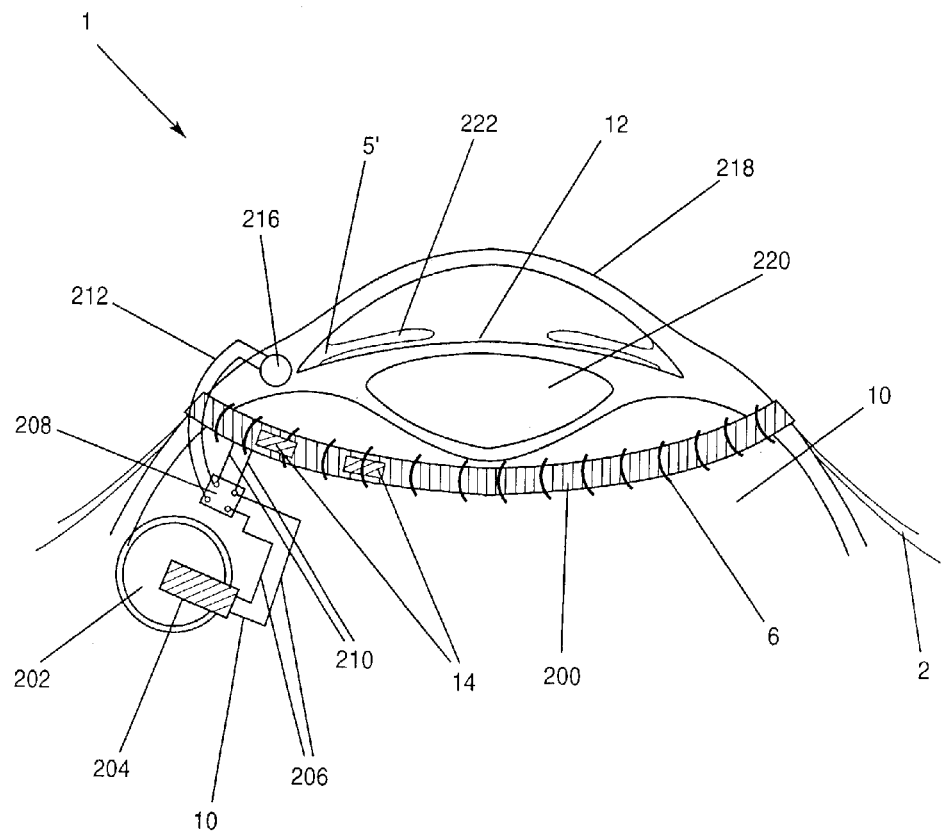
FIG. 18 is a transparent view of the front portion of an eye showing the ciliary muscle, the eye lens, the zonular fibers, the cornea, the smart band, the sensor, the relay and logic control unit and the battery.

Referring to FIG. 18, the transparent side view of eye 1 includes the extraocular muscles 2, cornea 218, lens 220, iris muscles 222, active scleral band 200 sutured to the sclera 10 over the ora serrata region by means of sutures 6. The artificial muscle sensor 202 is bonded to the ciliary muscle 204 and wired, by means of a first pair of wires 206, to a solid-state relay and logic control unit 208 which is bonded to the sclera 10 and connected to the active scleral band 200 by means of second electrical wire 210. The small implantable and transcutaneously rechargeable battery 216 which is bonded to sclera 10 and connected to the active scleral band 200 by means of second electrical wires 210 and connected to the relay and logic control unit 208 by means of third electrical wires 212.

The operation of the embodiment of FIGS. 17 and 18 is that upon near vision accommodation the ciliary muscle 204 contracts and causes the bonded artificial muscle sensor 202 to send a voltage signal of a few millivolts to the solid-state relay and logic control unit 208 by means of conducting wires 206. The solid-state relay and logic control unit 208, in turn, switches on the wires 210 and 212, thus energizes the active scleral band 200 by means of conducting wires 210 and 212. Active scleral band 200 constricts the ora serrata region causing the eye length and corneal curvature to increase and allow for near vision accommodation automatically. Once ciliary muscles 204 relax, the signal from the sensor 202 approaches a zero value and the solid-state relay and logic control unit 208 switches off battery 216 from energizing active band 200 and the band relaxes allowing the eye to return to normal vision.

Figure 19:
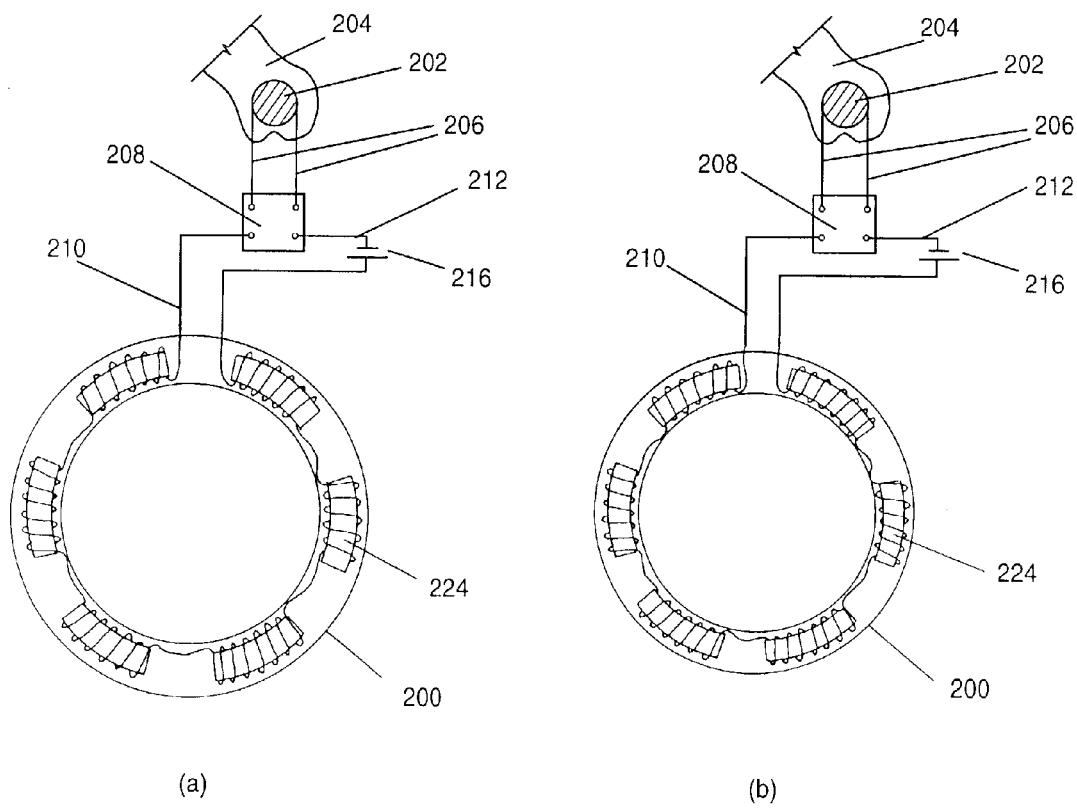
FIG. 19(a) is a schematic view of the active scleral band before activation or before ciliary muscle contraction.
FIG. 19(b) is a schematic view of the active scleral band after activation or after ciliary muscle contraction.

Referring to FIGS. 19(a) and 19(b) show another embodiment of an active scleral band. In this embodiment, active scleral band 200, which is made from active artificial muscle like structures, such as an assembly of embedded electromagnets 224 activates the active scleral band 200. The remaining components and operation are similar to the embodiment of FIGS. 17 and 18.

Figure 20:
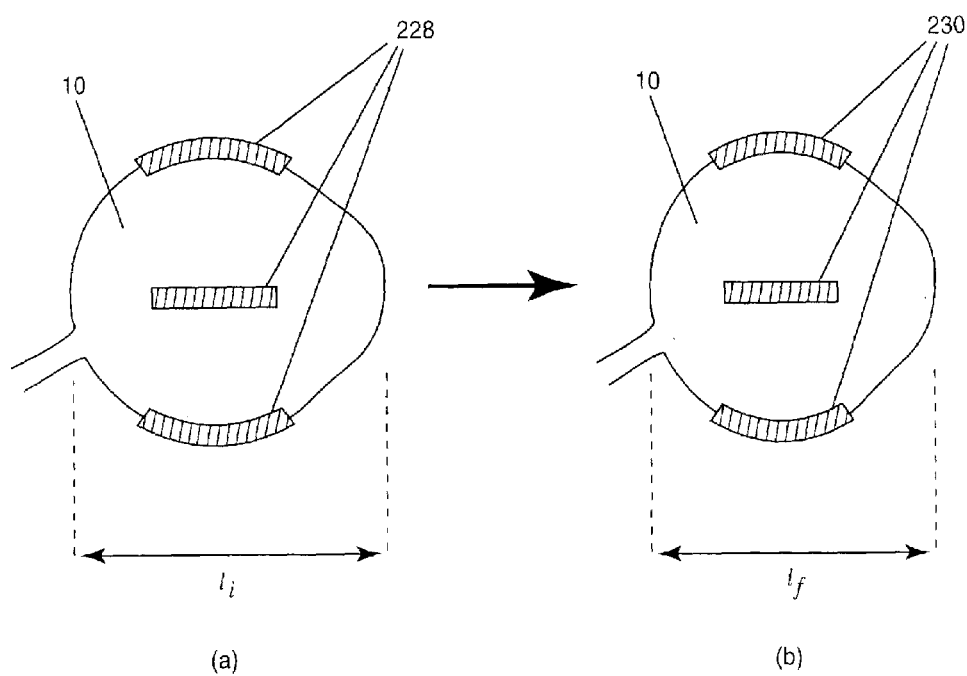
FIG. 20(a) is a schematic view of the scleral segments or ribs made with artificial muscles or heat shrink materials sutured or bonded to the sclera in an unactivated state for inducing tension in the sclera to create a length or curvature change.
FIG. 20(b) is a schematic view of the scleral segments or ribs made with artificial muscles or heat shrink materials sutured or bonded to the sclera in an activated state for inducing local tension in the sclera to create a length or curvature change.

Referring to FIG. 20(a) note that the scleral segments or ribs 228 made with artificial muscles or heat shrink materials for inducing local tension in the sclera 10 to create a length or curvature change, are in an unactivated state and the eye length is $I_i$.

Referring to FIG. 20(b) note that the scleral segments or ribs 230 made with artificial muscles or heat shrink materials for inducing local tension in the sclera 10 to create a length or curvature change, are in an activated state and thus cause the eye length to change to $I_f$ and corneal curvature to change to correct refractive errors due to myopia.

To surgically implant any of the embodiments described herein, the preferred surgical procedure can be performed. One of the following surgical procedures is necessary. A 360-degree conjunctiva peritomy is performed. The conjunctiva is carefully dissected free from the sclera. Each of the extraocular muscles are isolated and freed from the check ligaments. The composite artificial muscle constricting and/or expanding band is then placed underneath the extraocular muscles and then secured together creating a 360 degree band encircling the sclera. The band tension is adjusted in order to achieve emmetropia using an A-scan (ultrasonic determination of eye length and correct vision). The band is then secured to the sclera using a locking mechanism as well as 6.0 nylon sutures, or the like. In the alternative, the artificial muscle band can be placed 3 mm from the sclera and the band implanted one half thickness into the sclera. The simplest method of implantation is similar to the method used for scleral buckle surgery. The two alternative positions will increase the axial length of the globe. The active composite artificial muscle will deactivate on command returning the axial length to its original position, and vision back to normal (emmetropic vision).

In the case of heat shrink band, to correct presbyopia or hyperopia, the band is mildly heated to shrink constrict it to the right tension to cause the right expansion of the eye ball to achieve the right vision power or diopter as examined by an A-scan instrument, on the fly. In the alternative procedure, a 360 degree conjunctiva peritomy is performed. The conjunctiva is carefully dissected free form the sclera. An artificial muscle band is then placed 3 mm from the sclera, preferably over ora serrata or the limbus. The band is then implanted one half thickness into the sclera or sutured to the sclera.

The procedures above are brief descriptions of the possible sites of implantation to induce length change by the constriction or expansion of the scleral buckle tire/artificial muscle structure smart band. The advantage of this technology is that it is an active mechanism to be implemented when one is reading. The artificial muscle will deactivate on command returning the axial length to its original position.

Other patients that can use such active artificial muscle bands or segments are cataract patients after replacement of their lens with intraocular lens (IOL). In these patients the ability to accommodate is gone because the IOL is fairly inflexible and thus an active band will allow such patients to change their eye length and curvature to make accommodation corrections on demand. Finally, retinal detachment patients after surgery can use these bands for as long as it takes for their retina to reattach to sclera under the buckle pressure by healing. Once the detachment is repaired and healed the band can in fact be deactivated or taken out and the scleral buckle relaxed to enable the patients to go back to normal vision. Presently such patients suffer from induced unnecessary myopia due to the scleral buckle band constriction even after the detachment is healed.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

The invention claimed is:

1. An apparatus for actively constricting and expanding the sclera of a human eye, the apparatus comprising:

a band, said band comprising a heat shrink material, configured to be affixed around the sclera of the eye globe, said band comprising a means for actively inducing changes in an eye length and curvature of the cornea, said means for actively inducing comprising an automatic actuator.

2. The invention of claim 1 wherein said means for inducing changes comprises a means for increasing said eye length.

3. The invention of claim 1 wherein said means for inducing changes comprises a means for decreasing said eye length.

4. The invention of claim 1 wherein said automatic actuator comprises a heat source.

* * * * *